(12) United States Patent
Gruber et al.

(10) Patent No.: US 6,369,070 B1
(45) Date of Patent: Apr. 9, 2002

(54) METHODS FOR INHIBITING MRP1

(75) Inventors: Joseph M. Gruber, Brownsburg; Julian S Kroin; Bryan H Norman, both of Indianapolis, all of IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/646,062

(22) PCT Filed: Apr. 7, 1999

(86) PCT No.: PCT/US99/07613

§ 371 Date: Sep. 13, 2000

§ 102(e) Date: Sep. 13, 2000

(87) PCT Pub. No.: WO99/51228

PCT Pub. Date: Oct. 14, 1999

Related U.S. Application Data

(60) Provisional application No. 60/081,080, filed on Apr. 8, 1998.

(51) Int. Cl.[7] .................. A61K 31/4355; A61K 31/437; C07D 413/04
(52) U.S. Cl. .......................................... 514/293; 546/83
(58) Field of Search .............................. 546/83; 514/293

(56) References Cited

U.S. PATENT DOCUMENTS

| | | | |
|---|---|---|---|
| 4,588,731 A | * 5/1986 | Humbert et al. | 514/293 |
| 5,717,092 A | 2/1998 | Armistead et al. | 544/129 |
| 5,744,485 A | 4/1998 | Zelle et al. | 514/318 |

OTHER PUBLICATIONS

W. Steinschifter, et al., Synthesis of Oxazolo [4,5–c]quinolones by Themolytic Degradatrion of 4–Azido–2 (1H)–quinolones [1], *J. Heterocyclic Chem.*, 31, pp. 1647–1652, (1994).

* cited by examiner

*Primary Examiner*—Alan L. Rotman
*Assistant Examiner*—Rita Desai
(74) *Attorney, Agent, or Firm*—Kirby W. Lee; Elizabeth A. Dawalt

(57) ABSTRACT

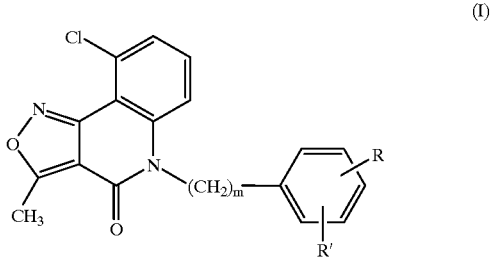

The present invention relates to a compound of formula (I), which is useful for inhibiting resistant neoplasms where the resistance is conferred in part or in total by MRP1.

18 Claims, No Drawings

METHODS FOR INHIBITING MRP1

This application is derived from a provisional application, Ser. No. 60/081,080, filed Apr. 8, 1998.

This application is a 371 of a PCT/US99/7613 filed Jun. 7, 1999.

Along with surgery and radiotherapy, chemotherapy continues to be an effective therapy for many cancers. In fact, several types of cancer are now considered to be curable by chemotherapy and include Hodgkin's disease, large cell lymphoma, acute lymphocytic leukemia, testicular cancer and early stage breast cancer. Other cancers such as ovarian cancer, small cell lung and advanced breast cancer, while not yet curable, are exhibiting positive response to combination chemotherapy.

One of the most important unsolved problems in cancer treatment is drug resistance. After selection for resistance to a single cytotoxic drug, cells may become cross resistant to a whole range of drugs with different structures and cellular targets, e.g., alkylating agents, antimetabolites, hormones, platinum-containing drugs, and natural products. This phenomenon is known as multidrug resistance (MDR). In some types of cells, this resistance is inherent, while in others, such as small cell lung cancer, it is usually acquired.

Such resistance is known to be multifactorial and is conferred by at least two proteins: the 170 kDa P-glycoprotein (MDR1) and the more recently identified 190 kDa multidrug resistance protein (MRP1). Although both MDR1 and MRP1 belong to the ATP-binding cassette superfamily of transport proteins, they are structurally very different molecules and share less than 15% amino acid homology. Despite the structural divergence between the two proteins, by 1994 there were no known consistent differences in the resistance patterns of MDR1 and MRP1 cell lines. However, the association, or lack thereof, of MRP1 and resistance to particular oncolytics is known. See Cole, et. al., "Pharmacological Characterization of Multidrug Resistant MRP-transfected Human Tumor Cells", Cancer Research, 54:5902–5910, 1994. Doxorubicin, daunorubicin, epirubicin, vincristine, and etoposide are substrates of MRP1, i.e., MRP1 can bind to these oncolytics and redistribute them away from their site of action, the nucleus, and out of the cell. Id. and Marquardt, D., and Center, M. S., *Cancer Research*, 52:3157, 1992.

Doxorubicin, daunorubicin, and epirubicin are members of the anthracycline class of oncolytics. They are isolates of various strains of Streptomyces and act by inhibiting nucleic acid synthesis. These agents are useful in treating neoplasms of the bone, ovaries, bladder, thyroid, and especially the breast. They are also useful in the treatment of acute lymphoblastic and myeloblastic leukemia, Wilm's tumor, neuroblastoma, soft tissue sarcoma, Hodgkin's and non-Hodgkin's lymphomas, and bronchogenic carcinoma.

Vincristine, a member of the vinca alkaloid class of oncolytics, is an isolate of a common flowering herb, the periwinkle plant (*Vinca rosea* Linn). The mechanism of action of vincristine is still under investigation but has been related to the inhibition of microtubule formation in the mitotic spindle. Vincristine is useful in the treatment of acute leukemia, Hodgkin's disease, non-Hodgkin's malignant lymphomas, rhabdomyosarcoma, neuroblastoma, and Wilm's tumor.

Etoposide, a member of the epipodophyllotoxin class of oncolytics, is a semisynthetic derivative of podophyllotoxin. Etoposide acts as a topoisomerase inhibitor and is useful in the therapy of neoplasms of the testis, and lung.

It is presently unknown what determines whether a cell line will acquire resistance via a MDR1 or MRP1 mechanism. Due to the tissue specificity of these transporters and/or in the case where one mechanism predominates or is exclusive, it would be useful to have a selective inhibitor of that one over the other. Furthermore, when administering a drug or drugs that are substrates of either protein, it would be particularly advantageous to coadminister an agent that is a selective inhibitor of that protein. It is, therefore, desirable to provide compounds which are selective inhibitors of MDR1 or MRP1.

The present invention relates to a compound of formula I:

where:

R is $(CH_2)_{m'}CHR^1NHR^2$, $O(CH_2)_2NHR^2$, $(CH_2)_{m'}COR^3$, $NHR^2$, and $(CH_2)_{m'}CHR^1NR^4R^5$;

R' is hydrogen, hydroxy, or $O(C_1-C_6$ alkyl optionally substituted with phenyl or $C_3-C_7$ cycloalkyl);

m and $m^1$ are independently at each occurrence 0, 1, or 2;

R' is independently at each occurrence hydrogen or $C_1-C_6$ alkyl;

$R^2$ is hydrogen, $COR^6$, $CH_2R'$, $SO_2R^7$, or a moiety of the formula $$-\overset{S}{\underset{\|}{C}}-NHR^7;$$

$R^3$ is hydrogen, hydroxy, $C_1-C_6$ alkoxy, an amino ester, an amino acid, or $NR^4R^5$;

$R^4$ is hydrogen or $C_1-C_6$ alkyl;

$R^5$ is hydrogen, $C_1-C_6$ alkyl, $C_6-C_{10}$ bicycloalkyl, $CH_2CH(CH_3)$phenyl, $CH(CH_3)CH_2CO_2R^1$, aryl, substituted aryl, $(CH_2)_nCHR^8NHC(O)OC(CH_3)_3$, $(CH_2)_nNH_2$, $(CH_2)_2NHCOR^6$, $(CH_2)_2OH$, $(CH_2)_q$-heterocycle, $(CH_2)_q$-substituted heterocycle, or $R^4$ and $R^5$ combine to form a pyrrolidin-1-yl, piperidin-1-yl, hexamethyleneimin-1-yl, or morpholin-4-yl ring;

n is 1, 2, 3, or 4;

q is 0, 1, 2, or 3;

$R^6$ is $C_1-C_6$ alkyl, substituted $C_3-C_6$ cycloalkyl, aryl, substituted aryl, tert-butoxy, $(CH_2)_q$-heterocycle, $(CH_2)_q$-substituted heterocycle, $(CH_2)_nS(O)_rR^1$, $C(CH_3)_2CH_2N(R^1)_2$, $(CH_2)_nCHR^8NHC(O)OC(CH_3)_3$, $(CH_2)_nNCHR^8NH_2$, $(CH_2)_2NH$-aryl, or $NHR^7$;

$R^{6'}$ is $C_1-C_6$ alkyl, substituted $C_3-C_6$ cycloalkyl, aryl, substituted aryl, $(CH_2)_q$-heterocycle, $(CH_2)$ q-substituted heterocycle, $(CH_2)_nS(O)_rR^1$, $C(CH_3)C_2CH_2N(R^{1)})_2$, $(CH_2)_nCHR^8NH-C(O)OC(CH_3)_3$, $(CH_2)_nCHR^8NH_2$, or $(CH_2)_2NH$-aryl;

r is 0, 1, or 2;

$R^7$ is $C_1-C_6$ alkyl, phenyl, or substituted phenyl; and $R^8$ is hydrogen or $CO_2R^1$; or a pharmaceutical salt or solvate thereof.

The present invention further relates to a method of inhibiting MRP1 in a mammal which comprises administering to a mammal in need thereof an effective amount of a compound of formula I, or a pharmaceutical salt or solvate thereof.

In another embodiment, the present invention relates to a method of inhibiting a resistant neoplasm, or a neoplasm susceptible to resistance in a mammal which comprises administering to a mammal in need thereof an effective amount of a compound of formula I, or a pharmaceutical salt or solvate thereof, in combination with an effective amount of an oncolytic agent.

The present invention also relates to a pharmaceutical formulation comprising a compound of formula I, or a pharmaceutical salt or solvate thereof, in combination with one or more oncolytics, pharmaceutical carriers, diluents, or excipients therefor.

The current invention concerns the discovery that a select group of compounds, those of formula I, are selective inhibitors of multidrug resistant protein (MRP1) and are thus useful in treating MRP1 conferred multidrug resistance (MDR) in a resistant neoplasm and a neoplasm susceptible to resistance.

The terms "inhibit" as it relates to MRP1 and "inhibiting MRP1" refer to prohibiting, alleviating, ameliorating, halting, restraining, slowing or reversing the progression of, or reducing MRP1's ability to redistribute an oncolytic away from the oncolytic's site of action, most often the neoplasm's nucleus, and out of the cell.

As used herein, the term "effective amount of a compound of formula I" refers to an amount of a compound of the present invention which is capable of inhibiting MRP1. The term "effective amount of an oncolytic" refers to an amount of oncolytic capable of inhibiting a neoplasm, resistant or otherwise.

The term "inhibiting a resistant neoplasm, or a neoplasm susceptible to resistance" refers to prohibiting, halting, restraining, slowing or reversing the progression of, reducing the growth of, or killing resistant neoplasms and/or neoplasms susceptible to resistance.

The term "resistant neoplasm" refers to a neoplasm which is resistant to chemotherapy where that resistance is conferred in part, or in total, by MRP1. Such neoplasms include, but are not limited to, neoplasms of the bladder, bone, breast, lung(small-cell), testis, and thyroid and also includes more particular types of cancer such as, but not limited to, acute lymphoblastic and myeloblastic leukemia, Wilm's tumor, neuroblastoma, soft tissue sarcoma, Hodgkin's and non-Hodgkin's lymphomas, and bronchogenic carcinoma.

A neoplasm which is "susceptible to resistance" is a neoplasm where resistance is not inherent nor currently present but can be conferred by MRP1 after chemotherapy begins. Thus, the methods of this invention encompass a prophylactic and therapeutic administration of a compound of formula I.

The term "chemotherapy" refers to the use of one or more oncolytics where at least one oncolytic is a substrate of MRP1. A "substrate of MRP1" is an oncolytic that binds to MRP1 and is redistributed away from the oncolytics site of action, (the neoplasm's nucleus) and out of the cell, thus, rendering the therapy less effective.

The terms "treat" or "treating" bear their usual meaning which includes preventing, prohibiting, alleviating, ameliorating, halting, restraining, slowing or reversing the progression, or reducing the severity of MRP1 derived drug resistance in a multidrug resistant tumor.

In the general formulae of the present document, the general chemical terms have their usual meanings. For example, the term "$C_1$–$C_4$ alkyl" refers to methyl, ethyl, propyl, isopropyl, cyclopropyl, butyl, cyclobutyl, s-butyl, and t-butyl. The term "$C_1$–$C_6$ alkyl" refers to a monovalent, straight, branched, or cyclic saturated hydrocarbon containing from 1 to 6 carbon atoms and includes $C_1$–$C_4$ alkyl groups in addition, $C_1$–$C_6$ alkyl also includes, but is not limited to, cyclopentyl, pentyl, hexyl, cyclohexyl, and the like. The term "$C_3$–$C_6$ cycloalkyl" refers to cyclopropyl, cyclobutyl, cyclopentyl, and cyclohexyl. The term "$C_5$–$C_7$ cycloalkyl" refers to cyclopentyl, cyclohexyl, and cycloheptyl. The term "$C_6$–$C_{10}$ bicycloalkyl" refers to bicyclo-[2.1.1] hexanyl, [2.2.1]heptanyl, [3.2.1]octanyl, [2.2.2]octanyl, [3.2.2]nonanyl, [3.3.1]nonanyl, [3.3.2]decanyl, and [4.3.1] decanyl ring system where the ring is connected to the parent molecular moiety at any point available for substitution on the ring.

The terms "$C_1$–$C_4$ alkoxy" and "$C_1$–$C_6$ alkoxy" refer to moieties of the formula O-($C_1$–$C_4$ alkyl) and O-($C_1$–$C_6$ alkyl) respectively.

The term "substituted $C_3$–$C_6$ cycloalkyl" refers to a $C_3$–$C_6$ cycloalkyl substituted once with a phenyl, substituted phenyl, or $CO_2R^1$ group.

The term "halo" or "halide" refers to fluoro, chloro, bromo, and iodo.

The term "aryl" refers to phenyl, benzyl, and napthyl.

The terms "substituted aryl" refers to a phenyl, benzyl, and napthyl group respectively substituted from 1 to 5 times independently with $C_1$–$C_6$ alkyl, halo, hydroxy, trifluoromethyl, $N(R^1)_2$, $SO_2N(R^1)_2$, NH—Pg, $C_1$–$C_6$ alkoxy, benzyloxy, $CO_2R^1$, $C_5$–$C_7$ cycloalkyl, trifluoromethoxy, or nitro.

The term "heterocycle" refers to a monovalent, saturated, unsaturated, or aromatic mono cyclic or fused ring system of 5 to 7 or 8 to 10 total atoms respectively containing from 1 to 3 heteroatoms selected independently from oxygen, sulfur, and nitrogen.

The term "substituted heterocycle" refers to a heterocycle ring substituted 1 or 2 times independently with a $C_1$–$C_6$ alkyl, halo, benzyl, phenyl, trifluoromethyl, or an oxo group.

The term "amino acid" as used in this specification refers to an N-terminally connected glycine, valine, methionine, phenylalanine, tryptophane, proline, aspartic acid, and glutamic acid.

The term "amino ester" as used in this specification refers to an amino acid where the carboxy group(s) of each (aspartic acid and glutamic acid each have two while the rest contain only one carboxy group) are substituted with a $C_1$–$C_6$ alkyl group. That is, the alkyl group when taken together with the carboxy group form a $C_1$–$C_6$ alkyl ester.

The term "protecting group" refers to an amino protecting group or a hydroxy protecting group. The species of protecting group will be evident from whether the "Pg" group is attached to a nitrogen atom (amino protecting group) or attached to an oxygen atom (hydroxy protecting group).

The term "amino protecting group" as used in this specification refers to a substituent(s) of the amino group commonly employed to block or protect the amino functionality while reacting other functional groups on the compound. Examples of such amino-protecting groups include the formyl group, the trityl group, the phthalimido group, the acetyl group, the trichloroacetyl group, the chloroacetyl, bromoacetyl, and iodoacetyl groups, urethane-type blocking groups such as benzyloxycarbonyl, 9-fluorenylmethoxycarbonyl ("FMOC"), and the like; and like amino protecting groups. The species of amino protecting group employed is not critical so long as the derivitized amino group is stable to the condition of subsequent reaction(s) on other positions of the molecule and can be removed at the appropriate point without disrupting the remainder of the molecule. Similar amino protecting groups used in the cephalosporin, penicillin, and peptide arts are also embraced by the above terms. Further examples of groups referred to by the above terms are described by T. W. Greene, Protective Groups in Organic Synthesis", John Wiley and Sons, New York, N.Y., 1991, Chapter 7 hereafter referred to as "Greene". A preferred amino protecting group is t-butyloxycarbonyl.

The term "hydroxy protecting group" denotes a group understood by one skilled in the organic chemical arts of the type described in Chapter 2 of Greene. Representative hydroxy protecting groups include, for example, ether groups including methyl and substituted methyl ether groups such as methyl ether, methoxymethyl ether, methylthiomethyl ether, tert-buylthiomethyl ether, (phenyldimethylsilyl) methoxy-methyl ether, benzyloxymethyl ether, p-methoxybenzyloxy-methyl ether, and tert-butoxymethyl ether; substituted ethyl ether groups such as ethoxyethyl ether, 1-(2-chloroethoxy)-ethyl ether, 2,2,2-trichloroethoxymethyl ether, and 2-(trimethylsilyl)ethyl ether; isopropyl ether groups; phenyl and substituted phenyl ether groups such as phenyl ether, p-chlorophenyl ether, p-methoxyphenyl ether, and 2,4-dinitrophenyl ether; benzyl and substituted benzyl ether groups such as benzyl ether, p-methoxybenzyl ether, o-nitrobenzyl ether, and 2,6-dichlorbenzyl ether; and alkylsilyl ether groups such as trimethyl- triethyl- and triisopropylsilyl ethers, mixed alkylsilyl ether groups such as dimethylisopropylsilyl ether, and diethylisopropylsilyl ether; and ester protecting groups such as formate ester, benzylformate ester, mono- di- and trichloroacetate esters, phenoxyacetate ester, and p-chlorophenoxyacetate and the like. The species of hydroxy protecting group employed is not critical so long as the derivatized hydroxy group is stable to the conditions of subsequent reaction(s) on other positions of the intermediate molecule and can be selectively removed at the appropriate point without disrupting the remainder of the molecule including any other hydroxy protecting group(s).

The term "carbonyl activating group" refers to a substituent of a carbonyl that renders that carbonyl prone to nucleophilic addition. Suitable activating groups are those which have a net electron withdrawing effect on the carbonyl. Such groups include, but are not limited to, alkoxy, aryloxy, nitrogen containing aromatic heterocycles, or amino groups such as oxybenzotriazole, imidazolyl, nitrophenoxy, pentachlorophenoxy, N-oxysuccinimide, N,N'-dicyclohexylisoure-O-yl, N-hydroxy-N-methoxyamino, and the like; acetates, formates, sulfonates such as methanesulfonate, ethanesulfonate, benzenesulfonate, or p-toluenylsulfonate, and the like; and halides especially chloride, bromide, or iodide.

In general, the term "pharmaceutical" when used as an adjective means substantially non-toxic to living organisms. For example, the term "pharmaceutical salt" as used herein, refers to salts of the compounds of formula I which are substantially non-toxic to living organisms. See, e.g., Berge, S. M, Bighley, L. D., and Monkhouse, D. C., "Pharmaceutical galts", *J. Pharm. Sci.*, 66:1, 1977. Typical pharmaceutical salts include those salts prepared by reaction of the compounds of formula I with an inorganic or organic acid or base. Such salts are known as acid addition or base addition salts respectively. These pharmaceutical salts frequently have enhanced solubility characteristics compared to the compound from which they are derived, and thus are often more amenable to formulation as liquids or emulsions.

Examples of pharmaceutical acid addition salts are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, glycollate, tartrate, methanesulfonate, ethanesulfonate, propanesulfonate, naphthalene-1-sulfonate, napththalene-2-sulfonate, mandelate, and the like of a compound of formula I.

Examples of pharmaceutical base addition salts are the ammonium, lithium, potassium, sodium, calcium, magnesiu, methylamino, diethylamino, ethylene diamino, cyclohexylamino, and ethanolamino salts, and the like of a compound of formula I.

The term "solvate" represent s an aggregate that comprises one or more molecules of the solute, such as a formula I compound, with one or more molecules of solvent.

The term "suitable solvent" refers to a solvent which is inert to the ongoing reaction and sufficiently solubilezes the reactants to effect the desired reaction. Examples of suitable solvents include but are not limited to, dichloromethane, chloroform, 1,2-dichloroethane, diethyl ether, acetonitrile, ethyl acetate, 1,3-dimethyl-2-imidazolidinone, tetrahydrofuran, dimethyltormamide, toluene, chlorobenzene, dimethylsulfoxide, mixtures thereof, and the like.

The term "carbonyl activating reagent" refers to a reagent that converts the carbonyl of a carboxylic acid group to one that is more prone to nucleophilic addition and includes, but is not limited to, such reagents as those found in "The Peptides", Gross and Meienhofer, Eds., Academic Press (1979), Ch. 2 and M. Bodanszky, "Principles of Peptide Synthesis", $2^{nd}$ Ed., Springer-Verlag Berlin Heidelberg, 1993, hereafter referred to as "The Peptides" and "Peptide Synthesis" respectively. Specifically, carbonyl activating reagents include nucleophilic sources of a halogen such as, thionyl bromide, thionyl chloride, oxalyl chloride, and the like; alcohols such as nitrophenol, pentachlorophenol, and the like; amines such as N-hydroxy-N-methoxyamine and the like; acid halides such as acetic, formic, methanesulfonic, ethanesulfonic, benzenesulfonic, or p-tolylsulfonic acid halide, and the like; and compounds such as 1,1'-carbonyldiimidazole, benzotriazole, imidazole, N-hydroxysuccinimide, dicyclohexylcarbodiimide, and the like.

The term "suitable thermodynamic base" refers to a base which acts as a proton trap for any protons which may be produced as a byproduct of the desired reaction or to a base which provides a reversible deprotonation of an acidic substrate and is reactive enough to effect the desired reaction without significantly effecting any undesired reactions. Examples of thermodynamic bases include, but are not limited to, carbonates, bicarbonates, and hydroxides (e.g., lithium, sodium, or potassium carbonate, bicarbonate, or hydroxide), tri-($C_1$–$C_4$ alkyl)amines, or aromatic nitrogen containing heterocycles (e.g., pyridine).

While all of the compounds of the present invention are useful, certain of the compounds are particularly interesting and are preferred. The following listing sets out several groups of preferred compounds, formulations, and methods. It will be understood that each of the listings may be combined with other listings to create additional groups of preferred embodiments.

a) m is 0 and m' is 0;

b) m is 0 and m' is 1;

c) R is at the meta position;

d) R is CHR¹NHR² and R¹ is methyl;
e) R is COR³;
f) R is (CH₂)COR³;
g) R is (CH₂)NR⁴R⁵;
h) R' is hydrogen;
i) R² is 4-aminosulfonylbenzyl;
j) R² is 3,4,5-trimethoxybenzyl;
k) R³ is (3,4,5-trimethoxyphenyl)amino;
l) R³ is (4-aminosulfonylphenyl)amino;
m) R³ (6-methoxyquinolin-8-yl)amino;
n) R⁴ is hydrogen;
o) R⁵ 5-methylisoxazol-3-oyl;
p) R⁵ is 3,4,5-trimethoxybenzoyl;
q) R⁵ 3,5-dimethoxy-4-hydroxybenzoyl;
r) R⁵ is 3,4,5-trimethoxybenzyl;
s) The compound is a pharmaceutical salt;
t) The compound is the hydrochloride;
u) The compounds of the Examples section;
v) The method where the mammal is a human;
w) The method where the oncolytic(s) is selected from: doxorubicin, daunorubicin, epirubicin, vincristine, and etoposide;
x) The method where the neoplasm is of the Wilm's type, bladder, bone, breast, lung(small-cell), testis, or thyroid or the neoplasm is associated with acute lymphoblastic and myeloblastic leukemia, neuroblastoma, soft tissue sarcoma, Hodgkin's and non-Hodgkin's lymphomas, or bronchogenic carcinoma; and
y) The formulation where the oncolytic(s) is selected from the group: doxorubicin, daunorubicin, epirubicin, vincristine, and etoposide.

The compounds of the present invention can be prepared by a variety of procedures, some of which are illustrated in the Schemes below. The particular order of steps required to produce the compounds of formula I is dependent upon the particular compound being synthesized, the starting compound, and the relative lability of the substituted moieties.

Compounds of formula I may be prepared from compounds of formula II as illustrated in Scheme 1 below where R, R', and m are as described supra.

Scheme 1

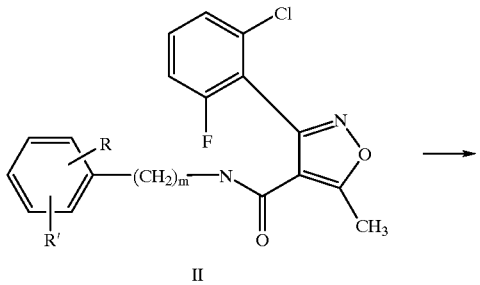

II

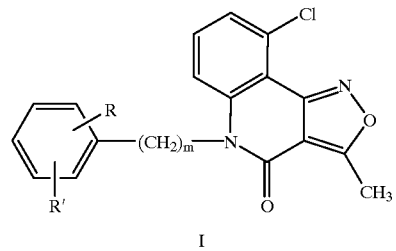

I

Compounds of formula I may be prepared by dissolving or suspending a compound of formula II in a suitable solvent and adding a suitable thermodynamic base. Typically a preferred and convenient solvent is dimethylformamide. Usually a convenient and preferred thermodynamic base is sodium hydroxide added as a 2N solution in methanol. The reactants are typically combined at room temperature but the resulting solution is typically heated to from about 30° C. to about the reflux temperature of the mixture for from 30 minutes to about 18 hours. Preferably, the mixture is heated to at least 50° C. for from about 1 to about 6 hours, and is most preferably heated to from about 65° C. to about 75° C. for from about 1.5 hours to about 3 hours. The base is typically employed in a large molar excess, usually in about a 4 to about an 8 molar excess relative to the compound of formula II. Preferably, about a 5 to about a 7 molar excess is typically employed. Certain intermediates, discussed below, of compounds of formula I may also be prepared by the method discussed above.

Any hydroxy or amino protecting groups found in the cyclized compound of formula I may optionally be removed as taught in Greene to provide the free amino or free hydroxy compounds of formula I. Preferred choices of protecting groups and methods for their removal may be found in the Preparations and Examples sections below.

Compounds of formula I where R is (CH₂)ₘCHR¹NHR², (CH₂)ₘ'CHR¹NR⁴R⁵, or O(CH₂)₂NHR² and R² is CH₂R⁶' may be prepared from compounds of formula I(a), I(c), or I(e) as illustrated in Scheme 2 below where R⁹ is a carbonyl activating group, and m, m', R', R¹, R², R⁴, R⁵, and R⁶' are as described supra.

Scheme 2

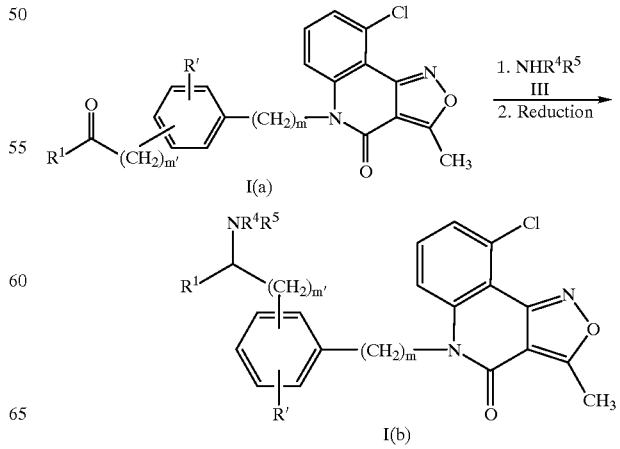

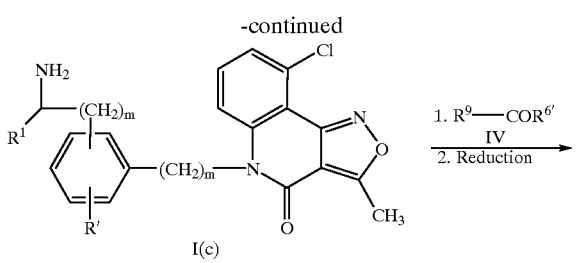

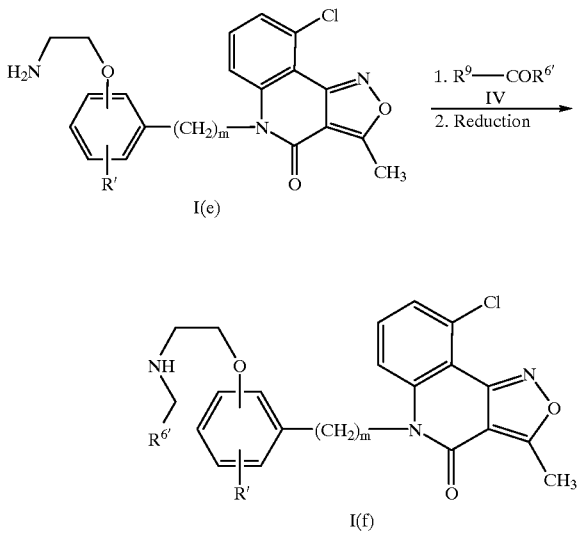

Compounds of formula I(a), I(c), or I(e) prepared as described in Scheme 1, may be converted to other compounds of the invention For example, the compounds of formula I(a), I(c), and I(d) may be reductively aminated to form the compounds of formula I(b), I(d), and I(f) respectively. Reductive aminations are well known transformations, see, e.g., Larock, "Comprehensive Organic Transformations", pg. 421, VCH Publishers, New York, N.Y., 1989, hereafter referred to as "Larock". In the context of the current invention, the reductive amination may be accomplished via standard solution or combinatorial synthetic techniques.

Compounds of formula III, I(c), or I(e) may be dissolved or suspended in a suitable solvent, optionally in the presence of a suitable thermodynamic base, and a compound of formula I(a) or IV is added to provide an imine intermediate. A Lewis acid catalyst, such as titanium(IV) isopropoxide, may also optionally be employed in order to promote this reaction. Once it is determined that the compound of formula I(a) or IV has been substantially consumed, the imine intermediate is typically reacted in situ with a suitable reducing agent to provide respectively the compounds of formula I(b), I(d), or I(f). The overall conversion may be performed at about 0° C. to the boiling point of the mixture but room temperature is a preferred reaction temperature. The individual steps of the formation of the imine and the reduction of the imine to the amine may take from 15 minutes to 24 hours. Imine formation is usually substantially complete in from 15 minutes to an hour while reduction of the imine is usually complete in from 30 minutes to 2 hours. Methanol is typically a preferred solvent.

A thermodynamic base is typically employed when the compound of formula III, I(c), or I(e) is an acid addition salt in order to convert the salt to its free amine form. Preferred thermodynamic bases for this purpose are N-methylmorpholine and triethylamine. A preferred Lewis acid catalyst is titanium(IV) isopropoxide. Suitable reducing agents include, but are not limited to, hydrogen over palladium or platinum on carbon, borane or complexes of borane, e.g., borane-pyridine, borane-t-butylamine, and borane-dimethylamine complex; borohydride reducing agents such as sodium borohydride or sodium cyanoborohydride; and lithium aluminum hydride. Sodium cyanoborohydride is a preferred reducing agent.

The compound of formula III, I(c), or I(e) is typically employed in a slight stoichiometric excess. For example, 1.01 to about 1.5 equivalents, relative to the compound of formula I(a) or IV respectively, is generally employed while 1.05 to about 1.15 equivalents is a preferred amount. The reducing agent is preferably employed in a stoichiometric amount relative to the compound of formula I(a) or IV but a slight excess, from 1.01 to 1.05 equivalents, is acceptable.

Compounds of formula I where R is $(CH_2)_{m'}CHR^1NHR^2$ or $O(CH_2)_2NHR^2R^2$ is $COR^6$, $SO_2R^7$ or a moiety of the formula

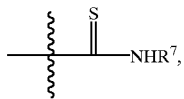

may be prepared from compounds of formula I(c) and I(e) as illustrated in Scheme 3 below where $R^{10}$ is $COR^6$, $SO_2R^7$, or a moiety of the formula

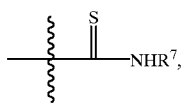

$R^{11}$ is O or S, and m, m', R', $R^1$, $R^6$, $R^{6'}$, $R^7$, and $R^9$ are as described supra.

Scheme 3

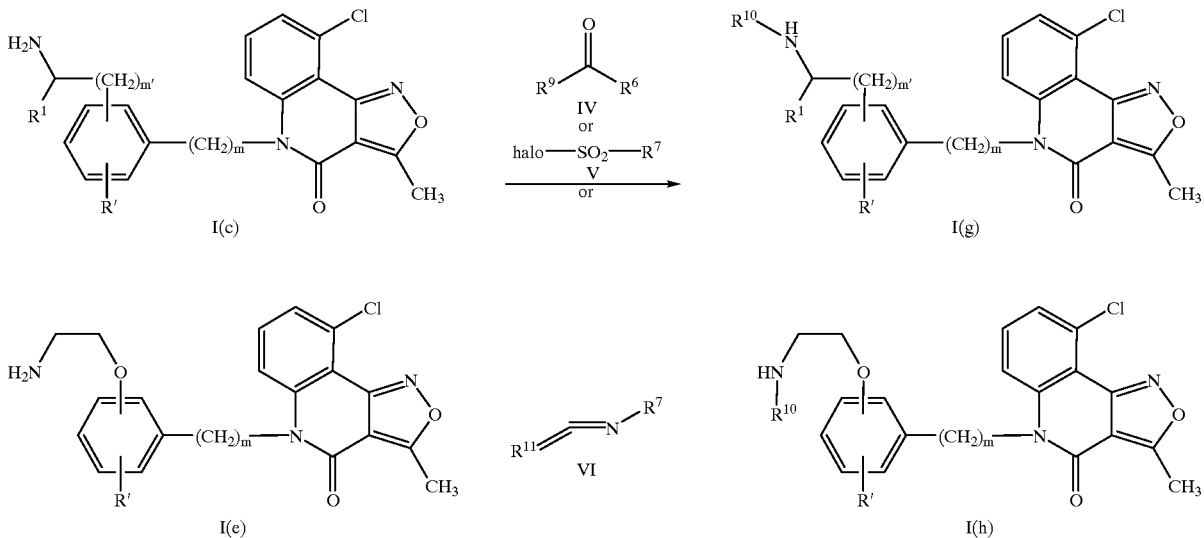

Compounds of formula I(c) and I(e) may be converted to other compounds of the invention via standard solution or combinatorial synthetic techniques. For example, a compound of formula I(c) or I(e) dissolved or suspended in a suitable solvent, optionally in the presence of a thermodynamic base, may be treated with a compound of formula IV to provide a compound of formula I(g) or I(h) where $R^{10}$ is $COR^6$. Typically a preferred and convenient solvent is dichloromethane. When a base is employed, triethylamine is typically a preferred base. Furthermore, when a base is employed, the base and compound of formula IV are typically employed in a slight stoichiometric excess. For example a 1.01 to 1.40 molar excess, relative to the compound of formula I(c) or I(e), is generally employed. About 1.15 to about 1.25 molar excess is typically preferred. When a base is not employed, the compound of formula IV is typically employed in a relatively larger stoichiometric excess. For example, about a 1.5 to about a 3 molar excess, relative to the compound of formula I(c) or I(e), is usually employed. About 1.8 to about 2.2 molar excess is typically preferred. The reaction is usually performed at a temperature range of about 0° C. to about the reflux temperature of the solvent for from 10 minutes to 18 hours. Preferably, the reaction is performed at about 15° C. to about 40° C. for from 5 minutes to about 1 hour.

Under the same conditions as the previous paragraph, a compound of formula I(c) or I(e) may alternatively be treated with a compound of formula V or VI to afford the compounds of formula I where R is $(CH_2)_{m'}CHR^1NHR^2$ or $O(CH_2)_2NHR^2$ and $R^2$ is $CONHR^7$, $SO_2R^7$ or a moiety of the formula

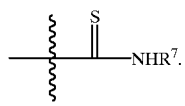

Compounds of formula I where R is $(CH_2)_{m'}COR^3$ and $R^3$ is $C_1-C_6$ alkoxy, an amino ester, or $NR^4R^5$ may be prepared from compounds of formula I(i) as illustrated in Scheme 4 below where $R^{12}$ is $NR^4 R^5$, an amino ester, or $C_1-C_6$ alkoxy, and m, m', R', $R^4$, $R^5$, and $R^9$ are as described supra

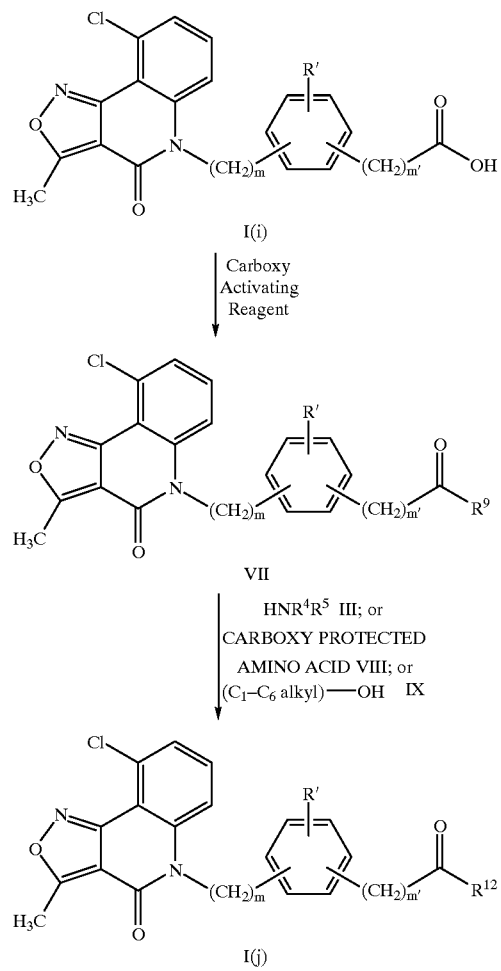

Compounds of formula I(i), prepared as described in Scheme 1, may also be converted to other compounds of the invention via solution or solid phase synthetic techniques. For example, acids of formula I(i) may be activated to form the activated carboxylic acids of formula VII by methods well known in the chemical arts. See, e.g., The Peptides, Peptide Synthesis and the Examples and Preparations sections below.

Generally, preparation of compounds of formula I(j) where $R^{12}$ is $NR^4R^5$ or an amino ester is performed in a manner similar to the reaction of compounds of formula I(c) or I(e) and IV described in Scheme 3. Specifically, such compounds of formula I(k) may be prepared by dissolving or suspending a compound of formula VII in a suitable solvent, optionally in the presence of a suitable thermodynamic base, and adding an amine of formula III or VIII. Typically a preferred and convenient solvent is dichloromethane. Preferred bases are triethylamine and piperidinylmethylpolystyrene resin. The amine is typically employed in a molar excess. For example, about a 1.5 to about a 3 molar excess, relative to the compound of formula VIII, is usually employed. About 1.8 to about 2.2 molar excess is typically preferred. The reaction is usually performed in a temperature range of about 0° C. to about the reflux temperature of the solvent for from 10 minutes to 18 hours. Preferably, the reaction is performed at about 15° C. to about 40° C. for from 5 minutes to about 2.5 hours.

Alternatively, the compound of formula I(i) may be activated and the addition of a compound of formula III, VIII, or IX may be performed in a one pot process as described in Example 41 below.

The compounds of formula I(j) where $R^{12}$ is $C_1$–$C_6$ alkoxy may be prepared by methods very well known in the chemical arts. For instruction on the conversion of activated carboxylic acids to esters see, e.g., Larock at 978–979. Alternatively, these compounds of formula I(j) may be prepared directly from the acids of formula I(i) as taught in the Larock reference at pages 966–972 or as disclosed in the Examples section below.

The pharmaceutical salts of the invention are typically formed by reacting a compound of formula I with an equimolar or excess amount of acid or base. The reactants are generally combined in a mutual solvent such as diethylether, tetrahydrofuran, methanol, ethanol, isopropanol, benzene, and the like for acid addition salts, or water, an alcohol or a chlorinated solvent such as dichloromethane for base addition salts. The salts normally precipitate out of solution within about one hour to about ten days and can be isolated by filtration or other conventional methods.

Acids commonly employed to form pharmaceutical acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, ethanesulfonic acid, oxalic acid, p-bromophenylsulfonic acid, carbonic acid, succinic acid, citric acid, tartaric acid, benzoic acid, acetic acid, and the like. Preferred pharmaceutical acid addition salts are those formed with mineral acids such as hydrochloric acid, hydrobromic acid, and sulfuric acid, and those formed with organic acids such as maleic acid, tartaric acid, and methanesulfonic acid.

Bases commonly employed to form pharmaceutical base addition salts are inorganic bases, such as ammonium or alkali or alkaline earth metal hydroxides, carbonates, bicarbonates, and the like. Such bases useful in preparing the salts of this invention thus include sodium hydroxide, potassium hydroxide, ammonium hydroxide, potassium carbonate, sodium carbonate, sodium bicarbonate, potassium bicarbonate, calcium hydroxide, calcium carbonate, and the like. The potassium and sodium salt forms are particularly preferred.

It should be recognized that the particular counterion forming a part of any salt of this invention is not of a critical nature, so long as the salt as a whole is pharmacologically acceptable and as long as the counterion does not contribute undesired qualities to the salt as a whole.

The starting materials and compounds of the present invention which are intermediates to other compounds of the present invention may be obtained by a number of routes. For example, compounds of formula II, I(a), I(c), I(e), and I(i) may be prepared according to the route shown in Scheme 5 where R, R', and m are as described supra.

Scheme 5

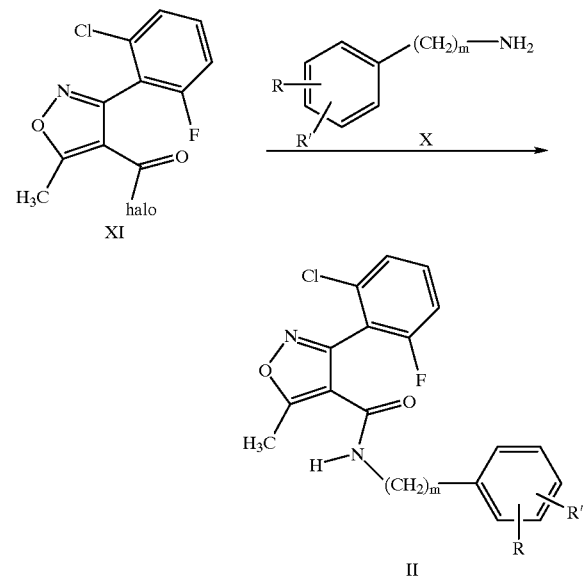

Compounds of formula II may be prepared by dissolving or suspending a compound of formula X in a suitable solvent and adding a compound of formula XI and a suitable thermodynamic base. Dichloromethane is a convenient solvent and is typically preferred. Pyridine is usually the preferred thermodynamic base. This amide forming reaction is also preferably run in the presence of dimethylamino pyridine (DMAP). The compound of formula XI is typically and preferably employed in an eguimolar amount, relative to the compound of formula X, but a slight excess (about a 0.05 to about 0.15 molar excess) is acceptable. The thermodynamic base is typically employed in a slight molar excess. For example, about a 1.01 to about a 1.2 molar excess, relative to the compound of formula X, is typically employed. About a 1.05 to about 1.15 molar excess is generally preferred. The DMAP is employed in a catalytic fashion. For example, about 5 molar percent to about 15 molar percent, relative to the compound of formula X, is typically employed. A 10 molar percent is usually preferred.

Compounds of formula X where R is $(CH_2)_{m'}COR^1$, $(CH_2)_{m'}NHPg$, $O(CH_2)_2NH$—Pg, or $(CH_2)_{m'}CO_2(C_1$–$C_6$ alkyl) which are used to prepare compounds of formula I(a), I(c), I(e), and I(i) respectively, are well known in the art and to the extent not commercially available, are readily synthesized by standard procedures commonly employed in the art. For example, these compounds of formula X may be prepared by reduction of the corresponding commercially available nitro compounds. Methods of reducing a nitro group to an amine are well known. See, e.g., Larock at 412–415 or in the Preparations and Examples sections below. In addition, compounds of formula X where R is $O(CH_2)_2NH$—Pg may be prepared from commercially available nitrophenols or nitrobenzyl alcohols as described in Preparations 15 and 16 below. Furthermore, the transformations described in Schemes 2–5 may be performed before the cyclization described in Scheme 1 to provide the compounds of formula X with a fully elaborated R substituent.

Compounds of formula III, IV, V, VI, VIII, IX, X, and XI are known in the art and, to the extent not commercially available, are readily synthesized by standard procedures commonly employed in the art.

The optimal time for performing the reactions of Schemes 1–5 can be determined by monitoring the progress of the reaction via conventional chromatographic techniques. Furthermore, it is preferred to conduct the reactions of the invention under an inert atmosphere, such as, for example, argon, or, particularly, nitrogen. Choice of solvent is generally not critical so long as the solvent employed is inert to the ongoing reaction and sufficiently solubilizes the reactants to effect the desired reaction. The compounds of formula II, I(a), I(c), I(e), and I(i) are preferably isolated and purified before their use in subsequent reactions. These compounds may crystallize out of the reaction solution during their formation and then collected by filtration, or the reaction solvent may be removed by extraction, evaporation, or decantation. These intermediates and final products of formula I may be further purified, if desired by common techniques such as recrystallization or chromatography over solid supports such as silica gel or alumina.

The skilled artisan will appreciate that not all substitutents are compatible with all reaction conditions, for example, compounds of the invention where R' is hydroxy. These compounds may be protected as the corresponding benzyl ether, and then converted to the hydroxy derivative at a convenient point in the synthesis by hydrogenolysis or other methods well known in the art.

The following Preparations and Examples are provided to better elucidate the practice of the present invention and should not be interpreted in any way as to limit the scope of same. Those skilled in the art will recognize that various modifications may be made while not departing from the spirit and scope of the invention. All publications mentioned in the specification are indicative of the level of those skilled in the art to which this invention pertains. The terms and abbreviations used in the instant Preparations and Examples have their normal meanings unless otherwise designated. For example "° C.", "N", "mmol", "g", "mL", "M", "HPLC", "IR", "MS(FD)", "MS(IS)", "MS(FIA)", "MS (FAB)", "MS(EI)", "UV", and "$^1$H NMR", refer to degrees Celsius, normal or normality, millimole or millimoles, gram or grams, milliliter or milliliters, molar or molarity, high performance liquid chromatography, infra red spectrometry, field desorption mass spectrometry, ion spray mass spectrometry, flow injection analysis mass spectrometry, fast atom bombardment mass spectrometry, electron impact mass spectrometry, ultraviolet spectrometry, and proton nuclear magnetic resonance spectrometry respectively. In addition, the absorption maxima listed for the IR spectra are only those of interest and not all of the maxima observed.

PREPARATIONS

Preparation 1

N-(5-Methylisoxaz-3-oyl)-3-Nitrobenzylamine

A solution containing 500 mg (2.65 mmol) of 3-nitrobenzylamine in 20 mL of dichloromethane was stirred at room temperature as 463 mg (3.18 mmol) of 5-methyl-3-isoxazoyl chloride was added. To this solution was added 0.92 mL (6.62 mmol) of triethylamine. The reaction was stirred an additional 1 hour at room temperature, diluted with 75 mL of ethyl acetate and the organic phase washed with 1N aqueous hydrochloric acid (twice), water (twice) and saturated aqueous sodium bicarbonate (thrice). The resulting organic solution was dried over sodium sulfate, filtered, and concentrated to give 550 mg (79%) of the title compound as a yellow solid. MS(FD) m/z 261 (M+).

Preparation 2

N-(5-Methylisoxaz-3-oyl)-3-Aminobenzylamine

To a solution containing 260 mg (1.00 mmol) of N-(5-methylisoxaz-3-oyl)-3-nitrobenzylamine in 20 mL of tetrahydrofuran was added 674 mg (3.00 mmol) of tin chloride dihydrate, followed by 2 ml of concentrated hydrochloric acid. The reaction was stirred at room temperature for 18 hours and then diluted with 100 mL of ethyl acetate. The organic solution was washed with saturated aqueous sodium bicarbonate, dried over sodium sulfate, filtered, and concentrated to give 200 mg (86%) of the title compound as a yellow foam. MS(FD) m/z 231 (M+).

Preparation 3

N-(5-Methylisoxaz-3-oyl)-N'-(5-Methyl-3-(2-Chloro-6-Fluorophenylisoxaz-4-oyl)-3-Aminobenzylamine To a solution containing 413 mg (1.78 mmol) of N-(5-methylisoxaz-3-oyl)-3-aminobenzylamine in 50 mm of dichloromethane was added 538 mg (1.96 mmol) of 3-(2-chloro-6-fluorophenyl)5-methyl-4-isoxazoyl chloride at room temperature. To this solution was added 0.157 mm (1.96 mmol) of pyridine, followed by 22 mg (0.18 mmol) of DMAP and the reaction was stirred at room temperature for 3 hours. The reaction was then diluted with 100 mL of ethyl acetate. This organic solution washed with 1N aqueous hydrochloric acid (twice), brine (twice) and saturated aqueous sodium bicarbonate solution (twice), dried over sodium sulfate, filtered, and concentrated in vacuo to yield 755 mg (90i) %f the title compound as a white solid. MS(FD) m/z 468 (M+).

Preparation 4

N-(5-Methylisoxaz-3-oyl)-2-Aminobenzylamine

2-Aminobenzylamine (490 mg, 4.01 mmol) and 5-methyl-3-isoxazoyl chloride (437 mg, 3.01 mmol) were converted to the title compound by the procedure of Preparation 1 to yield 250 mg. (36%). MS(FD) m/z 231 (M+). $^1$H NMR consistent with desired product.

Preparation 5

N-(5-Methylisoxaz-3-oyl)-N'-2-(2-Chloro-6-Fluorophenyl)-5-Methylisoxaz-4-oyl-2-Aminobenzylamine N-(5-Methylisoxaz-3-oyl)-2-aminobenzylamine (160 mg, 0.692 mmol) and 3-(2-chloro-6-fluorophenyl)5-methyl-4-isoxazoyl chloride (208 mg, 0.761 mmol) were converted to the title compound by the procedure of Preparation 3 to yield 275 mg. (85%). MS(FD) m/z 468 (M+). IR(KBr) υ=1669, 1612, 1590, 1455, 1250, 898 cm$^{-1}$.

Preparation 6

N-(5-Methylisoxaz-3-oyl)-4-Aminobenzylamine

4-Aminobenzylamine (265 mg, 2.17 mmol) and 5-methyl-3-isoxazoyl chloride (316 mg, 2.17 mmol) were converted to the title compound by the procedure of Preparation 1 except that a 2:1 mixture of mono to bis acylated products resulted which were separated by partitioning the mixture in 100 mL of ethyl acetate and 100 mL of 1N aqueous hydrochloric acid. The organic was extracted an additional two times with the acid and the combined acid extracts were made basic (about pH 8) with saturated aqueous sodium bicarbonate. This basic solution was extracted with ethyl acetate and the organic extracts were dried over magnesium sulfate, filtered, and concentrated to yield 94 mg of the monoacylated title compound. (18.7%). MS(FD) m/z 231 (M+). IR(KBr) υ=3334, 1646, 1551, 1519, 1459 cm$^{-1}$.

Preparation 7

N-(5-Methylisoxaz-3-oyl)-N'-2-(2-Chloro-6-Fluorophenyl)-5-Methylisoxaz-4-oyl-4-Aminobenzylamine N-(5-Methylisoxaz-3-oyl)-4-aminobenzylamine (74 mg, 0.32 mmol) and 3-(2-chloro-6-fluorophenyl)5-methyl-4-isoxaoyl chloride (96 mg, 0.35 mmol) were converted to the title compound by the procedure of Preparation 3 to yield 150 mg. (100%). MS(FD) m/z 468 (M+). IR(KBr) υ=3310, 1685, 1655, 1598, 1250 cm$^{-1}$.

Preparation 8

N-(5-Methyl-3-Phenylisoxaz-3-oyl)-3-Nitrobenzylamine

3-Nitrobenzylamine (500 mg, 2.65 mmol) and 3-phenyl-5-methyl-4-isoxazoyl chloride (705 mg, 3.18 mmol) were converted to the title compound by the procedure of Preparation 1 to give 750 mg. (83.9%). MS(FD) m/z 337 (M+). IR(KBr) v 3307, 1648, 1524, 1346 cm$^{-1}$.

Preparation 9

N-(5-Methyl-3-Phenylisoxaz-3-oyl)-3-Aminobenzylamine

N-(5-Methyl-3-phenylisoxaz-3-oyl)-3-nitrobenzylamine (650 mg, 1.92 mmol) was converted to the title compound by the procedure of Preparation 2 to yield 555 mg. (94.2%). MS(FD) m/z 307 (M+). IR(KBr) υ 3444, 1647, 1612, 1538, 1180 cm$^{-1}$.

Preparation 10

N-(5-Methyl-3-Phenylisoxaz-3-oyl)-N'-2-(2-Chloro-6-Fluorophenyl)-5- Methylisoxaz-4-oyl-3-Aminobenzylamine N-(5-Methyl-3-phenylisoxaz-3-oyl)-3-aminobenzylamine (555 mg, 1.81 mmol) and 3-(2-chloro-6-fluorophenyl)5-methyl-4-isoxazoyl chloride (96 mg, 1.81 mmol) were converted to the title compound by the procedure of Preparation 3 to give 465 mg. (47.2%). MS(FD) m/z 544 (M+). IR(KBr) υ 3284, 1653, 1610, 1533, 1443, 897 cm$^{-1}$.

Preparation 11

N-(5-Methyl-3-(2-Chloro-6-Fluorophenylisoxaz-4-oyl)-3-Aminoacetophenone

To a solution of 3-aminoacetophenone (4.0 g, 29.6 mmol) in dichloromethane (250 mL) under an atmosphere of nitrogen was added 4-dimethylaminopyridine (542 mg, 4.44 mmol) followed by the rapid dropwise addition of pyridine (7.2 mL, 88.8 mmol). After cooling to 0° C. a solution of 3-(2-chloro-6-fluorophenyl)-5-methylisoxazole-4-carbonyl chloride (8.48 g, 31.0 mmol) in dichloromethane (125 mL) was added dropwise over 1 hour. The ice bath was removed and the reaction mixture was allowed to stir for 4 hours. The reaction mixture was diluted with ethyl acetate (500 mL), and washed with 1N aqueous hydrochloric acid (3×125 mL), water (2×100 mL), and brine (3×75 mL). The ethyl acetate layer was dried (magnesium sulfate), and the volatiles were removed under reduced pressure to provide the title compound (11.79 g) which was used as is in subsequent reactions. $^1$H NMR(CDCl$_3$) δ 7.72–7.44 (m, 5H), 7.38 (dd, 1H, J=8 Hz), 7.27 (dd, 1H, J=8 Hz), 7.11 (br s, 1H), 2.86 (s, 3H), 2.57 (s, 3H).

Preparation 12

N-(t-Butyloxycarbonyl)-3-Nitrobenzylamine

To a suspension of 4-nitrobenzylamine hydrochloride (10.3 g, 54.7 mmol) and triethylamine (11.1 g, 109 mmol) in dichloromethane (75 mL) was added a solution of di-tert-butyldicarbonate (15.5 g, 71.1 mmol) in dichloromethane (25 L). After stirring overnight at room temperature, the reaction was washed with 10k citric acid (2×250 mL), dried over magnesium sulfate, filtered, and the solvent removed under reduced pressure. The residue was recrystallized from ethyl acetate/hexanes to afford the 13.80 g of the title compound. (100%).

Preparation 13

N-(t-Butyloxycarbonyl)-3-Aminobenzylamine

To a solution of N-(t-butyloxycarbonyl)-3-nitrobenzylamine (13.8 g, 54.7 mmol) in dimethylformamide (200 mL) was added tin(II) chloride dihydrate (74.1 g, 328 mmol) and the reaction was stirred at room temperature for 48 hours. The dimethylformamide was removed under vacuum. The residue was resuspended in dichloromethane (300 ml), washed with brine (200 mL), filtered through a celite pad, and the solvent removed to provide 12.2 g of the title compound. (100%).

Preparation 14

N-(t-Butyloxycarbonyl)-N'-(5-Methyl-3-(2-Chloro-6-Fluorophenylisoxaz-4-oyl)-3-Aminobenzylamine A solution of 3-(2-chloro-6-fluorophenyl)-5-methylisoxaz-4-oyl chloride (15 g, 54.7 mmol) in dichloromethane (25 mL) was added to a solution of N-(t-butyloxycarbonyl)-3-aminobenzylamine (12.2 g, 54.7 mmol) and triethylamine (13.8 g, 137 mmol) in dichloromethane (200 ml). After stirring overnight at room temperature, the reaction was washed with 10% citric acid (2×200 ml), dried over magnesium sulfate, filtered, and solvent was removed. The residue was purified by liquid chromatography (10 ethyl acetate/hexanes) to provide 18.96 g of the title compound. (75%).

Preparation 15

N-t-Butyloxycarbonyl-1-Aminoethoxy-3-Nitrobenzene

To a solution containing 3.0 g (21.6 mmol) of 3-nitrophenol in 100 mL of tetrahydrofuran was added 3.8 g (23.8 mmol) of N-(t-butyloxycarbonyl)-aminoethanol and 7.4 g (28.1 mmol) of triphenylphosphine at room temperature. To this solution was added 4.4 mL (28.1 mmol) of diethylazodicarboxylate (DEAD) dropwise with stirring. The resulting solution was stirred at room temperature for an additional 2 hours and then diluted with 200 mL of ethyl acetate. This organic solution was washed twice each with 1N aqueous sodium hydroxide, brine, and 1N hydrochloric acid, dried over sodium sulfate, filtered, and concentrated in vacuo to give a yellow oil. The residue was purified by flash chromatography on a silica gel column, using 50% ethyl acetate-hexanes as the eluent. The major fractions were combined and concentrated to give 5.50 g (90%) of title compound as a clear yellow oil. MS(FD) m/z 282 (M+).

Preparation 16

N'-t-Butyloxycarbonyl-2-Aminoethoxyaniline

To a solution of 3.00 g (10.6 mmol) of N-t-butyloxycarbonyl-1-aminoethoxy-3-nitrobenzene in 25 mL methanol was added 25 mg of 10% palladium on carbon. This mixture was subjected to hydrogenation at 30 psi of hydrogen on a Parr shaker for 15 hours. The mixture was subsequently filtered over celite and concentrated in vacuo to give 2.20 g (82%) of the title compound as a beige oil. MS(FD) m/z 252 (M+).

Preparation 17

N'-(t-Butyloxycarbonyl)-N-(5-Methyl-3-(2-Chloro-6-Fluorophenylisoxaz-4-oyl)-3-Aminoethoxyaniline A solution containing 2.00 g (7.93 mmol) of N'-t-butyloxycarbonyl-3-aminoethoxyaniline in 50 mL of dichloromethane was stirred at room temperature as 2.17 g (7.93 mmol) of 3-(2-chloro-6-fluorophenyl)5-methyl-4-isoxazoyl in chloride was added. To this solution:was added 0.70 mL (8.7 mmol) of pyridine, followed by 97 mg (0.79 mmol) of DMAP and the reaction was stirred at room temperature for 3 hours. The reaction was then diluted with 100 mL of ethyl acetate and this organic solution washed twice each with 1N aqueous hydrochloric acid, brine, and saturated aqueous sodium bicarbonate solution, dried over sodium sulfate, filtered, and concentrated in vacuo to yield 3.55 g (91%) of the title compound as a beige solid. MS(FD) m/z 489 (M+).

Preparation 18

Ethyl N-(5-Methyl-3-(2-Chloro-6-Fluorophenyl)isoxaz-4-oyl)-3-Aminobenzoate 3-(2-Chloro-6-fluorophenyl)5-methylisoxaz-4-oyl chloride (7.9 g, 29.0 mmol) was added in portions to a stirred solution of ethyl-3-aminobenzoate (4.0 g, 29.0 mmol) and triethylamine (4.04 mL, 29.0 mmol) in dry dichloromethane at 0° C. Following the final addition, the mixture was allowed to warm to ambient temperature and stir for 1 hour. The solution was washed with 0.5M aqueous hydrochloric acid, brine, aqueous sodium bicarbonate, dried over magnesium sulfate, filtered, and evaporated to a foam which was used in subsequent reactions without further purification.

Preparation 19

Methyl N-5-Methyl-3-(2-Chloro-6-Fluorophenyl)isoxaz-4-oyl)-3-Aminophenylacetate

A solution containing 1.93 g (11.7 mmol) of methyl 3-aminophenylacetate in 50 mL of dichloromethane was stirred at room temperature as 3.20 g (11.7 mmol) of 3-(2-chloro-6-fluorophenyl)5-methylisoxaz-4-oyl chloride was added. To this solution was added 1.03 mL (12.9 mmol) of pyridine, followed by 140 mg (1.17 mmol) of DMAP and the reaction was stirred at room temperature for 3 hours. The reaction was then diluted with 100 mL of ethyl acetate. This organic solution was washed with 1N aqueous hydrochloric acid (twice), brine (twice) and saturated aqueous sodium bicarbonate solution (twice), dried over sodium sulfate, filtered, and concentrated in vacuo to yield 4.45 g (94%) of the title compound as a pale yellow solid. MS(FD) m/z 402 (M+).

Preparation 20

3-(Isoxazolo[3,4-c]-1,2-Dihydro-3-methyl-6-chloroquinolin-2-on-1-yl)phenylacetyl Chloride To a solution containing 107 mg (0.290 mmol) of 3-(isoxazolo[3,4-c]-1,2-dihydro-3-methyl-6-chloroquinolin-2-on-1-yl)phenylacetic acid in 20 mL of dichloromethane was added 30

L (0.348 mmol) of oxalyl chloride at room temperature. The reaction was stirred at room temperature for 1 hour, and concentrated in vacuo to give the title compound as a white solid. This material was used without further purification.

Preparation 21

3-(Isoxazolo[3,4-c]-1,2-Dihydro-3-methyl-6-chloroquinolin-2-on-1-yl)benzoyl Chloride 3-(Isoxazolo[3,4-c]-1,2-dihydro-3-methyl-6-chloroquinolin-2-on-1-yl)benzoic acid was converted to the title compound by the procedure of Preparation 20.

Preparation 22

O-Methanesulfonyl-1-Nitro-3-(1-Hydroxyethyl)benzene

Sodium borohydride (343 mg, 9.08 mmol) was added in portions to a solution of 3-nitroacetophenone (5 g, 30.3 mmol) in methanol. Following the final addition the reaction mixture was allowed to stir for 1 hour and then the solvent was evaporated. The residue was partitioned between dichloromethane and deionized water. The organics were separated, dried over magnesium sulfate, filtered, and evaporated to a light brown gum. This was dissolved in dichloromethane containing triethylamine (4.2 ml, 30.3 mmol) and cooled in an ice bath. Mesyl chloride (2.34 ml, 30.3 mmol) was added dropwise, and after the final addition the reaction mixture was allowed to warm to ambient temperature and stirred overnight. The solution was washed sequentially with aqueous hydrochloric acid (0.5 M), aqueous sodium bicarbonate, brine, dried over magnesium sulfate, filtered, and evaporated to 6.5 g of the title compound which was used without further purification.

Preparation 23

1-Nitro-3-(1-Azidoethyl)benzene

O-Methanesulfonyl-1-nitro-3-(1-hydroxyethyl)benzene (3.1 g, 12.6 mmol) was dissolved in anhydrous dimethylsulfoxide and sodium azide (1.07 g, 16.4 mmol) added. The reaction mixture was allowed to stir for 18 hours, diluted with ethyl acetate, and washed several times with brine. The organics were then dried over magnesium sulfate, filtered, evaporated, and chromatographed (silica gel, 5:1 hexane-:ethyl acetate) to afford 2.9 g of the title compound.

Preparation 24

3-Nitro-α-Methylbenzylamine

1-Nitro-3-(1-azidoethyl)benzene (1.3 g, 6.76 mmol) was dissolved in tetrahydrofuran and triphenylphosphine (1.9 g, 7.4 mmol) was added. The resulting solution was stirred at ambient temperature for 18 hours. 1M aqueous sodium hydroxide (1 ml) was then added and the stirring continued for 48 hours. The reaction was diluted with ethyl acetate, washed with brine several times, dried over magnesium sulfate, filtered, and evaporated. The residue was chromatographed (silica gel, 2:1 hexane:ethyl acetate) to provide 1.1 g of the title compound. (99%). $^1$H NMR(CDCl$_3$)

1.41 (3H, d, J=6.7 Hz), 1.60 (2H, br s), 4.28 (1H, q, J=6.9 Hz), 7.50 (1H, t, J=7.7 Hz), 7.70 (1H, d, J=7.7 Hz), 8.09 (1H, d, J=7.7 Hz), 8.25 (1H, s).

Preparation 25

N-t-Butyloxycarbonyl-3-Nitro-α-Methylbenzylamine

To a suspension of 3-nitro-α-methylbenzylamine (1.12 g, 6.74 mmol) in dichloromethane (75 mL) was added a solution of di-tert-butyldicarbonate (1.76 g, 8.09 mmol) in dichloromethane (25 mL). After overnight stirring at room temperature, the reaction was washed with 10% citric acid (2×250 mL), dried over magnesium sulfate, filtered, and the solvent was removed under reduced pressure to afford the title compound which was used in subsequent reactions without further purification.

Preparation 26

N-t-Butyloxycarbonyl-3-Amino-α-Methylbenzylamine

To a solution of the N-t-butyloxycarbonyl-3-nitro-α-methylbenzylamine (1.79 g, 6.74 mmol) in dimethylformamide (50 1 mL) was added tin(II) chloride dihydrate (9.12 g, 40.4 mmol) and the reaction was stirred at room temperature for 48 hours. The dimethylformamide was removed under vacuum, residue resuspended in dichloromethane (100 ml), washed with brine (100 mL), filtered through a celite pad, and solvent removed to provide the crude aniline.

Preparation 27

N-(t-Butyloxycarbonyl)-N'-(5-Methyl-3-(2-Chloro-6-Fluorophenylisoxaz-4-oyl)-3-Amino-α-Methylbenzylamine A solution of 3-(2-chloro-6-fluorophenyl)-5-methylisoxaz-4-oyl chloride (1.85 g, 6.74 mmol) in dichloromethane (25 mL) was added to a solution of the aniline (1.59 g, 6.74 mmol) and triethylamine (2.04 g, 20.2 mmol) in dichloromethane (100 mL). After overnight stirring at room temperature, the reaction was washed with 10% citric acid (2×50 ml), dried over magnesium sulfate, filtered, and the solvent removed to afford the title compound which was used in subsequent reactions without further purification.

Preparation 28

N-(5-Methyl-3-(2-Chloro-6-Fluorophenylisoxaz-4-oyl)-3-Nitrobenzylamine

3-Nitrobenzylamine (511 mg, 2.71 mmol) and 3-(2-chloro-6-fluorophenyl)-5-methylisoxaz-4-oyl chloride (742 mg, 2.71 mmol) were suspended in 10 mL of dichloromethane and triethylamine was added (0.95 mL, 6.78 mmol). The reaction went clear and was stirred at room temperature for 2 hours. The reaction was then diluted with 100 mL of ethyl acetate and the organic layer was washed twice each with 1N aqueous hydrochloric acid and 1N aqueous sodium hydroxide. The organic layer was then dried over sodium sulfate, filtered, and concentrated in vacuo to give 1.12 g of the title compound. (>100). MS(IE) m/z 390 (M$^{+1}$). IR 3280, 1648, 1532, 1349, 1251 cm$^{-1}$.

Preparation 29

1-(3-Nitrobenzyl)-3-Isoxazolo[3,4-c]-1,2-Dihydro-3-Methyl-6-Chloroquinolin-2-one N-(5-Methyl-3-(2-chloro-6-fluorophenylisoxaz-4-oyl)-3-nitrobenzylamine (940 mg) was dissolved in 5 mL of dimethylformamide and 5 mL of 2N sodium hydroxide in methanol. The reaction was stirred at room temperature for 1 hour and additional dimethylformamide was added to dissolve precipitate that formed. The reaction was allowed to stir for an additional hour and then poured into 2N aqueous hydrochloric acid. This mixture was extracted with ethyl acetate several times. The combined extracts were washed with brine, dried over sodium sulfate, filtered, and concentrated in vacuo to provide 852 mg of the title compound. MS(IE) m/z 370 (M+1). IR 3306, 2952, 1718, 1638, 1547, 1211 cm$^{-1}$.

EXAMPLES

Example 1

1-(N-5-Methylisoxazol-3-oyl)-3-(Isoxazolo[3,4-c]-1,2-Dihydro-3-Methyl-6-Chloroquinolin-2-on-1-yl)benzylamine N-(5-Methylisoxaz-3-oyl)-N'-(5-methyl-3-(2-chloro-6-fluorophenylisoxaz-4-oyl)-3-aminobenzylamine (75 mg, 0.160 mmol) was dissolved in 10 mL of dimethylformamide and 5 mL of 2N sodium hydroxide in methanol. After 2 hours, the reaction was diluted with 50 mL of ethyl acetate. The resulting mixture was washed with twice each with 1N aqueous hydrochloric acid, sodium bicarbonate, and brine, dried over sodium sulfate, filtered, and concentrated. The residue was purified by flash chromatography (silica gel, 50% ethyl acetate-hexanes) to give 70 mg (97%) of the title compound as a white solid. MS(FD) m/z 448 (M+). IR(CHCl$_3$) υ 1685, 1632, 1597, 1458 cm$^{-1}$.

Example 2

1-(N-5-Methylisoxazol-3-oyl)-2-(Isoxazolo[3,4-c]-1,2-Dihydro-3-Methyl-6-Chloroquinolin-2-on-1-yl)benzylamine N-(5-Methylisoxaz-3-oyl)-N'-(5-methyl-3-(2-chloro-6-fluorophenylisoxaz-4-oyl)-2-aminobenzylamine (273 mg, 0.58 mmol) was converted to the title compound by the procedure of Example 1 except that the reaction time was 3 hours to give 200 mg (77%) as a yellow powder. MS(FD) m/z 448 (M+). IR(KBr)

682, 1631, 1596, 1455, 1320 cm$^{-1}$.

Example 3

1-(N-5-Methylisoxazol-3-oyl)-4-(Isoxazolo[3,4-c]-1, 2-Dihydro-3-Methyl-6-Chloroquinolin-2-on-1-yl) benzylamine N-(5-Methylisoxaz-3-oyl)-N'-(5-methyl-3-(2-chloro-6-fluorophenylisoxaz-4-oyl)-4-Aminobenzylamine (100 mg, 0.213 mmol) was converted to the title compound by the procedure of Example 1 except that the reaction time was about 15 minutes to give 59 mg (61%). MS(FD) m/z 448 (M+). IR(KBr) υ 1681, 1631, 1596, 1540, 1323 cm$^{-1}$.

Example 4

1-(N-3-Phenyl-5-Methylisoxazol-3-oyl)-3-(Isoxazolo[3,4-c]-1,2-Dihydro-3-Methyl-6-Chloroquinolin-2-on-1-yl)benzylamine N-(5-Methyl-3-phenylisoxaz-3-oyl)-N'-(5-methyl-3-(2-chloro-6-fluorophenylisoxaz-4-oyl)-3-aminobenzylamine (400 mg, 0.734 mmol) was converted to the title compound by the procedure of Example 1 except that the reaction time was about 18 hours to give 305 mg (796). MS(FD) m/z 524 (M+). IR(KBr) υ 3302, 1662, 1596, 1528, 1322 cm$^{-1}$.

Example 5

3-(Isoxazolo[3,4-c]-1,2-Dihydro-3-methyl-6-chloroquinolin-2-on-1-yl)acetophenone To a solution of N-(5-methyl-3-(2-chloro-6-fluorophenylisoxaz-4-oyl)-3-aminoacetophenone (29.6 mmol) in dimethylformamide (275 mL) was added sodium hydroxide (275 mL, 2N in methanol) and the reaction mixture was allowed to stir for 48 hours while monitoring by TLC. The reaction mixture was filtered and the filtrate was diluted with ethyl acetate (1.5 L). The ethyl acetate solution was washed with 1N aqueous hydrochloric acid (3×300 mL), water (2×250 mL), and brine (300 mL). The organic phase was dried (magnesium sulfate), and the volatiles were removed under reduced pressure. The crude residue was chromatographed (silica gel, 1.5–10% methanol/chloroform) to provide the title compound as a white solid (4.5 g, 43%), mp 78–81° C. $^1$H NMR(CDCl$_3$) δ 8.15 (d, 1H, J=8 Hz), 7.88 (s, 1H), 7.75 (dd, 1H, J=8 Hz), 7.51 (d, 1H, J=8 Hz), 7.36 (d, 1H, J=8 Hz), 7.26 (dd, 1 H, J=8 Hz), 6.50 (d, 1H, J=8 Hz), 2.92 (s, 3H), 2.64 (s, 3H). MS(FAB) 352.9 (M+1).

Example 6

3-(Isoxazolo[3,4-c]1,2-Dihydro-3-methyl-6-chloroquinolin-2-on-1-yl)aniline 3-(2-Chloro-6-fluorophenyl)-5-methylisoxazole-4-carbonyl chloride (7.6 g, 27.7 mmol) was added portionwise to a stirred solution of 1,3-phenylenediamine (3 g, 27.7 mmol) and triethylamine (4.25 ml, 30.5mmol) in anhydrous dichloromethane at 0° C. Following the final addition, the reaction mixture was stirred at ambient temperature for 2 hours. The precipitated solid was collected by filtration and washed with cold methanol to give an off white solid. The filter cake was suspended in a mixture of tetrahydrofuran and 1M sodium hydroxide in methanol (1:1 v/v) and stirred at ambient temperature for 20 hours. The mixture was cooled in ice, filtered and washed with ice-cold methanol, and dried to provide the 6.5 g of the title compound. (72%). MS(EI) 326 (M+1). $^1$H NMR(CDCl$_3$) 2.9 (3H, s), 3.9 (2H, br s), 6.55–6.85 (4H, m), 7.22–7.41 (3H, m).

Example 7

1-(N-t-Butyloxycarbonyl)-3-(Isoxazolo[3,4-c]-1,2-Dihydro-3-methyl-6-chloroquinolin-2-on-1-yl) benzylamine To a solution of N-(t-butyloxycarbonyl)-N'-(5-methyl-3-(2-chloro-6-fluorophenyl)isoxaz-4-oyl)-3-aminobenzylamine (19.0 g, 41.2 mmol) in dry dimethylformamide (200 mL) was added a solution of sodium hydroxide (8.24 g, 206 mmol) in methanol. After stirring overnight at room temperature, the reaction mixture was poured onto ice, the solid was removed by vacuum filtration and purified by liquid chromatography (10% ethyl acetate/hexanes) to afford 16.31 g of the title compound as a tan foam. (90%). MS(FAB) 440 (M+1). $^1$H NMR(CDCl$_3$) 1.55 (9H, s), 2.9 (3H, s), 4.4 (2H, d), 4.9–5.0 (1H, bs), 6.55 (1H, s), 7.15–7.65 (6H, s).

Example 8

3-(Isoxazolo[3,4-c]-1,2-Dihydro-3-methyl-6-chloroquinolin-2-on-1-yl)benzylamine 1-(N-t-butyloxycarbonyl)-3-(isoxazolo[3,4-c]-1,2-dihydro-3-methyl-6-chloroquinolin-2-on-1-yl)benzylamine (1.20 g, 2.73 mmol) was dissolved in 5 mL of trifluoroacetic acid and stirred at room temperature for 1 hour. The mixture was concentrated in vacuo and the residue azeotroped twice with chloroform to give 1.15 g of an amorphous solid. (93%). MS(FD) m/z 339 (M+ for free base). $^1$H NMR consistent with desired product.

Example 9

1-(N-3,5-Dimethoxy-4-Benzyloxybenzoyl)-3-(Isoxazolo[3,4-c]-1,2-Dihydro-3-methyl-6-chloroquinolin-2-on-1-yl)benzylamine 3,5-Dimethoxy-4-benzyloxybenzoic acid (317 mg, 1.10 mmol) was dissolved in dichloromethane and EDC (211 mg, 1.10 mmol) added. In a separate flask, 3-(isoxazolo[3,4-c]-1,2-dihydro-3-methyl-6-chloroquinolin-2-on-1-yl) benzylamine (333 mg, 0.734 mmol), N-methylmorpholine, and dichloromethane were mixed. Some dimethylformamide was then added to the solution containing the amine before combining it with the solution containing the activated ester. A catalytic amount of DMAP was then added and the resulting solution was stirred at room temperature for 18 hours. The reaction was diluted with ethyl acetate and washed twice each with 1N aqueous hydrochloric acid, 1N aqueous sodium hydroxide, and brine. The organic layer was concentrated to give 380 mg of the title compound as an amorphous solid (85%). MS(FIA) m/z 610.

Example 10

1-(N-3,4,5-Trimethoxybenzyl)-3-(Isoxazolo[3,4-c]-1,2-Dihydro-3-methyl-6-chloroquinolin-2-on-1-yl) benzylamine 3,4,5-Trimethoxybenzaldehyde (40 mg, 0.20 mmol) was dissolved in 2 mL dry methanol and N-methylmorpholine (25 μL, 0.22 mmol) and 3-(isoxazolo[3,4-c]-1,2-dihydro-3-methyl-6-chloroquinolin-2-on-1-yl)benzylamine (100 mg, 0.22 mmol) was added. The resulting solution was allowed to stir under nitrogen at room temperature for about 30 minutes. A precipitate formed. Methanol (2 mL) and sodium cyanoborohydride (13 mg, 0.20 mmol) were then added. After 1 hour, the precipitate was no longer visible. TLC (ethyl acetate) indicated completion of the reaction so the reaction was diluted with ethyl acetate and washed with 25 mL of saturated aqueous sodium bicarbonate and brine (3×25 mL). The organic layer was dried over sodium sulfate, filtered, and removed in vacuo. The residue was taken up in ethyl acetate and purified via silica gel chromatography (ethyl acetate) to give 90 mg of the title compound. (87%). MS(IS) m/z 518. EA calculated for $C_{28}H_{26}N_3O_5Cl$: C, 64.68; H, 5.04; N, 8.08. Found: C, 64.62; H, 5.16; N, 7.87.

Example 11

1-(N-3,5-Dimethoxy-4-Hydroxybenzoyl)-3-(Isoxazolo[3,4-c]-1,2-Dihydro-3-methyl-6-chloroquinolin-2-on-1-yl)benzylamine 1-(N-3,5-Dimethoxy-4-benzyloxybenzoyl)-3-(isoxazolo[3,4-c]-1,2-dihydro-3-methyl-6-chloroquinolin-2-on-1-yl)benzylamine (100 mg, 0.164 mmol) was added to thioanisole (19.2 mL, 0.164 mmol) and the resulting mixture was diluted with trifluoroacetic acid. The reaction was stirred at room temperature for 1 hour and then concentrated in vacuo. The residue was pumped on overnight using house vacuum. The crude resulting solid was purified via chromatography (silica gel, gradient 50–100% ethyl acetate:hexanes) to give the title compound. $^1$H NMR consistent with desired product. MS(FD) m/z 519 (M+).

Example 12

N-(3,4,5-Trimethoxyphenyl)-N-(3-(Isoxazolo[3,4-c]-1,2-Dihydro-3-methyl-6-chloroquinolin-2-on-1-yl)benzyl) urea 3-(Isoxazolo[3,4-c]-1,2-dihydro-3-methyl-6-chloroquinolin-2-on-1-yl)benzylamine (100 mg, 0.22 mmol) was suspended in dry dichloromethane and 25 μL of N-methylmorpholine added under nitrogen at room temperature. The reaction was sonicated and 1 mL of dry dimethylformamide was added. 3,4,5-Trimethoxyphenylisocyanate (48 mg, 0.23 mmol) was then added to the mixture and the resulting solution was allowed to stir for about 18 hours. The reaction was diluted with ethyl acetate and washed 3 times each with 1N aqueous hydrochloric acid and aqueous sodium bicarbonate, dried over sodium sulfate, and filtered. The filter cake was washed with methanol and the filtrate solvent was removed. The residue was taken up in dichloromethane/hexanes and recrystallized to give 59 mg of the title compound. 49%. MS(IS) 548 (M+). EA calculated for $C_{28}H_{25}ClN_4O_6$: C, 61.26; H, 4.59; N, 10.21. Found: C, 60.98; H, 4.87; N, 9.97.

Example 13

N-(3,4,5-Trimethoxyphenyl)-N-(3-(Isoxazolo[3,4-c]-1,2-Dihydro-3-methyl-6-chloroquinolin-2-on-1-yl)benzyl) thiourea 3-(Isoxazolo[3,4-c]-1,2-dihydro-3-methyl-6-chloroquinolin-2-on-1-yl)benzylamine (100 mg, 0.22 mmol) and 3,4,5-trimethoxyphenylisothiocyanate (52 mg, 0.22 mmol) were converted to the title compound by the procedure of Example 12 except that the product precipitated out of the reaction solution after stirring for about 18 hours, was filtered, and was not purified further to give 62 mg. 49%. $^1$H NMR(d DMSO) consistent with desired product. IR(KBr) 1679, 1635, 1576, 1525, 1502 cm$^{-1}$.

Example 14

1-(N-4-Methoxyphenylsulfonyl)-3-(Isoxazolo[3,4-c]-1,2-Dihydro-3-methyl-6-chloroquinolin-2-on-1-yl)benzylamine 3-(Isoxazolo[3,4-c]-1,2-dihydro-3-methyl-6-chloroquinolin-2-on-1-yl)benzylamine (50 mg, 0.147 mmol) was dissolved in 2 mL of dry dimethylformamide and stirred under nitrogen at room temperature. 4-Methoxybenzenesulfonyl chloride (30 mg, 0.147 mmol) was added followed by triethylamine (22 mg, 0.22 mmol) and the resulting mixture was stirred for about 18 hours. The reaction was diluted with ethyl acetate and washed 3 times each with 1N aqueous hydrochloric acid and brine, dried over sodium sulfate, filtered, and the solvent removed. The residue was treated with dichloromethane/hexanes to precipitate 57 mg of the title compound. (76%). EA calculated for $C_{25}H_{20}ClN_3O_5S$: C, 58.88; H, 3.95; N, 8.24. Found: C, 59.11; H, 4.01; N, 8.23. MS(IS) 510 (M+).

Example 15

1-(N-t-Butyloxycarbonyl)aminoethoxy-3-(Isoxazolo[3,4-c]-1,2-Dihydro-3-methyl-6-chloroquinolin-2-on-1-yl)benzene N'-(t-Butyloxycarbonyl)-N'-(5-methyl-3-(2-chloro-6-fluorophenylisoxaz-4-oyl)-3-aminoethoxyaniline (3.50 g, 7.14 mmol) was converted to the title compound by the procedure of Example 1 except that the reaction was performed at 70° C. and the crude product was purified by recrystallization from 50% ethyl acetate-isooctane to give 2.50 g (74%) as a white crystalline solid. MS(FD) m/z 469 (M+).

Example 16

1-Aminoethoxy-3-(Isoxazolo[3,4-c]-1,2-Dihydro-3-methyl-6-chloroquinolin-2-on-1-yl)benzene To a solution of 1-(N-t-butyloxycarbonyl)aminoethoxy-3-(isoxazolo[3,4-c]-1,2-dihydro-3-methyl-6-chloroquinolin-2-on-1-yl)benzene (1.00 g, 2.13 mmol) in 5 mL dichloromethane was added 5 mL of trifluoroacetic acid. The reaction was stirred at room temperature for 1 hour and concentrated in vacuo. The oily solid was dissolved in 30 mL of ethyl acetate and the organic solution was washed twice with 1N aqueous sodium hydroxide, dried over sodium sulfate, filtered, and concentrated to give 731 mg (93%) of the title compound as a white solid. MS(FD) m/z 369 (M+).

Example 17

1-(N-Benzoyl)aminoethoxy-3-(Isoxazolo[3,4-c]-1,2-Dihydro-3-methyl-6-chloroqulnolin-2-on-1-yl)benzene To a solution of 1-aminoethoxy-3-(isoxazolo[3,4-c]-1,2-dihydro-3-methyl-6-chloroquinolin-2-on-1-yl)benzene (100 mg, 0.270 mmol) in 5 mL of dichloromethane was added 35 μL (0.30 mmol) of benzoyl chloride followed by the addition of 45 μL (0.32 mmol) of triethylamine. The reaction was stirred at room temperature for 1 hour and then diluted with 25 mL of ethyl acetate. This organic solution was washed twice each with 1N aqueous hydrochloric acid, brine, and saturated aqueous sodium bicarbonate, dried over sodium sulfate, filtered, and concentrated in vacuo to give 105 mg (82%) of the title compound as a white amorphous solid. MS(FD) m/z 473 (M+).

Example 18

1-(N-3,4,5-Trimethoxybenzoyl)aminoethoxy-3-(Isoxazolo[3,4-c]-1,2-Dihydro-3-methyl-6-chloroquinolin-2-on-1-yl)benzene 3,4,5-Trimethoxybenzoyl chloride (69 mg, 0.297 mmol) and 1-aminoethoxy-3-(isoxazolo[3,4-c]-1,2-dihydro-3-methyl-6-chloroquinolin-2-on-1-yl)benzene (100 mg, 0.270 mmol) were converted to the title compound by the procedure of Example 17 to yield 120 mg (79%). MS(FD) m/z 563 (M+).

Example 19

1-(N-Acetyl)aminoethoxy-3-(Isoxazolo[3,4-c]-1,2-Dihydro-3-methyl-6-chloroquinolin-2-on-1-yl)benzene Acetyl chloride (21 μl, 0.297 mmol) and 1-aminoethoxy-3-(isoxazolo[3,4-c]-1,2-dihydro-3-methyl-6-chloroquinolin-2-on-1-yl)benzene (100 mg, 0.270 mmol) were converted to the title compound by the procedure of Example 17 to yield 98 mg (88%). MS(FD) m/z 411 (M+).

Example 20

1-(N-Methanesulfonyl)aminoethoxy-3-(Isoxazolo[3,4-c]-1,2-Dihydro-3-methyl-6-chloroquinolin-2-on-1-yl)benzene Methanesulfonyl chloride (23 ml, 0.297 mmol) and 1-aminoethoxy-3-(isoxazolo[3,4-c]-1,2-dihydro-3-methyl-6-chloroquinolin-2-on-1-yl)benzene (100 mg, 0.270 mmol) were converted to the title compound by the procedure of Example 17 to yield 91 mg (75%). MS(FD) m/z 447 (M+).

Example 21

1-(N-4-(N-Acetylamino)benzenesulfonyl)aminoethoxy-3-(Isoxazolo[3,4-c]-1,2-Dihydro-3-methyl-6-chloroquinolin-2-on-1-yl) benzene N-Acetylsulfanilyl chloride (63 mg, 0.270 mmol) and 1-aminoethoxy-3-(isoxazolo[3,4-c]-1,2-dihydro-3-methyl-6-chloroquinolin-2-on-1-yl)benzene (100 mg, 0.270 mmol) were converted to the title compound by the procedure of Example 17 to yield 91 mg (75%). MS(FD) m/z 565.9 (M+). IR(KBr) υ 1660, 1592, 1330, 1153 cm$^{-1}$.

Example 22

1-(N-1-Oxo-3-(2-Benzoxazolinon-3-yl)propyl)aminoethoxy-3-(Isoxazolo[3,4-c]-1,2-Dihydro-3-methyl-6-chloroquinolin-2-on-1-yl)benzene 3-(2-Benzoxazolinon-3-yl)propionic acid (317 mg, 0.405 mmol) was dissolved in 10 mL of tetrahydrofuran and hydroxybenztriazole hydrate (78 mg, 0.405 mmol) followed by 1-(3-dimethylaminopropyl)-3-ethylcarbodiumide hydrochloride (EDC) were added. In a separate flask, 1-aminoethoxy-3-(isoxazolo[3,4-c]-1,2-dihydro-3-methyl-6-chloroquinolin-2-on-1-yl)benzene (100 mg, 0.270 mmol) was dissolved in 5 mL of dimethylformamide and added to the reaction mixture followed by 2 mg of dimethylamino pyridine. The resulting solution was allowed to stir at room temperature for 18 hours. The reaction was diluted with 50 mL of ethyl acetate and washed twice each with 1N aqueous hydrochloric acid, brine, saturated aqueous sodium bicarbonate, and brine again. The organic layer was dried over magnesium sulfate, filtered, and concentrated to give 122 mg (81%) of the title compound. MS(FD) m/z 558 (M+).

Example 23

1-(N-1-Oxo-4-(N-t-Butyloxycarbonyl)amino-4-Carbomethoxybutyl)aminoethoxy-3-(Isoxazolo[3,4-c]-1,2-Dihydro-3-methyl-6-chloroquinolin-2-on-1-yl)benzene N-Boc-glutamic acid methyl ester (88 mg, 0.338 mmol) and 1-aminoethoxy-3-(isoxazolo[3,4-c]-1,2-dihydro-3-methyl-6-chloroquinolin-2-on-1-yl)benzene (100 mg, 0.270 mmol) were converted to the title compound by the procedure of Example 22 to yield 110 mg (66%). MS(FD) m/z 612 (M+).

Example 24

1-(N-1-Oxo-4-Amino-4-Carbomethoxybutyl)aminoethoxy-3-(Isoxazolo[3,4-c]-1,2-Dihydro-3-methyl-6-chloroquinolin-2-on-1-yl)benzene 1-(N-1-Oxo-4-(N-t-butyloxycarbonyl)amino-4-carbomethoxybutyl)aminoethoxy-3-(isoxazolo[3,4-c]-1,2-dihydro-3-methyl-6-chloroquinolin-2-on-1-yl)benzene was dissolved in 5 mL of trifluoroacetic acid and stirred at room temperature for I hour and concentrated to give 21 mg (100%) of the title compound. MS(FD) m/z 513 (M+).

Example 25

1-(N-1-Oxo-4-(N-t-Butyloxycarbonyl)amino-4-Carboxybutyl)aminoethoxy-3-(Isoxazolo[3,4-c]-1,2-Dihydro-3-methyl-6-chloroquinolin-2-on-1-yl)benzene 1-(N-1-Oxo-4-(N-t-butyloxycarbonyl)amino-4-carbomethoxybutyl)aminoethoxy-3-(isoxazolo[3,4-c]-1,2-dihydro-3-methyl-6-chloroquinolin-2-on-1-yl)benzene (77 mg, 0.13 mmol) was dissolved in 5 mL of 50% methanol in tetrahydrofuran and 5 mL of 2N aqueous sodium hydroxide was added. The resulting mixture was stirred at room temperature for 2 hours, acidified with 1N aqueous hydrochloric acid, and extracted three times with ethyl acetate. The organic layer was dried over magnesium sulfate, filtered, and concentrated to give the title compound. MS(FD) m/z 599 (M+).

Example 26

1-(N-1-Oxo-4-Amino-4-Carboxybutyl)aminoethoxy-3-(Isoxazolo[3,4-c]-1,2-Dihydro-3-methyl-6-chloroquinolin-2-on-1-yl)benzene 1-(N-1-Oxo-4-(N-t-butyloxycarbonyl)amino-4-carboxybutyl)aminoethoxy-3-(isoxazolo[3,4-c]-1,2-dihydro-3-methyl-6-chloroquinolin-2-on-1-yl)benzene (25 mg, 0.042 mmol) was dissolved in 1 mL of dichloromethane and 1 mL of trifluoroacetic acid was added. The resulting mixture was stirred at room temperature for 45 minutes and

Example 27

Ethyl 3-(Isoxazolo[3,4-c]-1,2-Dihydro-3-methyl-6-chloroquinolin-2-on-1-yl)benzoate Ethyl 3-(N-5-methyl-3-(N-2-chloro-6-fluorophenylisoxaz-4-oyl)aminobenzoate (4.5 g, 11.6 mmol) was dissolved in dry tetrahydrofuran and cooled in an ice bath. Sodium hydride (428 mg of 60% dispersion in oil) was added in portions. After the final addition, the mixture was allowed to warm to ambient temperature and stir for 18 hours. The reaction was quenched with saturated ammonium chloride and diluted with ethyl acetate. The organics were washed with brine, dried over magnesium sulfate, filtered, and evaporated to a yellow solid. The residue was suspended in hot ethyl acetate-hexanes, cooled, and filtered to provide 1.86 g of the title compound. MS(FAB) 383 (M+1).

Example 28

3-(Isoxazolo[3,4-c]-1,2-Dihydro-3-methyl-6-chloroquinolin-2-on-1-yl)benzoic Acid Ethyl 3-(isoxazolo[3,4-c]-1,2-dihydro-3-methyl-6-chloroquinolin-2-on-1-yl)benzoate(1.76 g, 4.60 mmol) was dissolved in 9:1 (v/v) tetrahydrofuran:methanol and cooled in an ice bath. A solution of lithium hydroxide hydrate (5.1 ml of a 1M solution in water) was added dropwise. The mixture was allowed to warm to ambient temperature and stir for 18 hours. After this period the tetrahydrofuran was evaporated (bath temp<40C). The aqueous residue was cooled in an ice bath and acidified by the dropwise addition of 2M aqueous hydrochloric acid. The solid which precipitated was collected by filtration and dried to yield 1.48 g of the title compound as a white solid. $^1$H (DMSO-d6) δ 2.8 (3H, s), 6.45 (1H, m), 7.4–7.48 (2H, m), 7.65 (1H, d, J=7.2 Hz), 7.68 (1H, t, J=7.2 Hz), 7.91 (1H, s), 8.11 (1H, d, J=7.2 Hz). EA calculated for $C_{18}H_{11}N_2O_4Cl0.8H_2O$: C, 58.56; H, 3.44; N, 7.59. Found C, 58.48; H, 3.42; N, 7.42.

Example 29

3-(Isoxazolo[3,4-c]-1,2-Dihydro-3-methyl-6-chloroquinolin-2-on-1-yl)benzoic Acid Methyl Ester 3-(Isoxazolo[3,4-c]-1,2-dihydro-3-methyl-6-chloroquinolin-2-on-1-yl)benzoyl chloride (50 mg, 0.134 mmol) was dissolved in 3 mL of dry dichloromethane and stirred under nitrogen at room temperature. 100 mL of dry methanol was added and reaction was stripped down on rotovap after 1 hour. The residue was taken up in ethyl acetate and washed with aqueous sodium bicarbonate and brine, dried over sodium sulfate, filtered, and treated with dichloromethane:hexanes to precipitate the product. After filtration, 42 mg of the title compound was obtained as an off white solid. (86%). This material was then recyrstallized from dichloromethane:hexanes. EA calculated for $C_{19}H_{13}ClN_2O_4$: C, 61.88; H, 3.55; N, 7.60. Found: C, 62.17; H, 3.65; N, 7.41. MS(FD) 368 (M+).

Example 30

N-3,4,5-Trimethoxyphenyl-3-(Isoxazolo[3,4-c]-1,2-Dihydro-3-methyl-6-chloroquinolin-2-on-1-yl)benzamide 3-(Isoxazolo[3,4-c]-1,2-dihydro-3-methyl-6-chloroquinolin-2-on-1-yl)benzoyl chloride (50 mg, 0.134 mmol) was dissolved in 3 mL of dry dichloromethane and stirred under nitrogen at room temperature. 3,4,5-Trimethoxy aniline (25 mg, 0.134 mmol) was added and reaction was stripped down on rotovap after 1 hour. The residue was taken up in ethyl acetate and washed with aqueous sodium bicarbonate and brine, dried over sodium sulfate, filtered, and concentrated to give 45 mg of the title compound. (86%). MS(FD+) 519. $^1$H NMR consistent with title compound.

Example 31

N-3,4,5-Trimethoxybenzyl-3-(Isoxazolo[3,4-c]-1,2-Dihydro-3-methyl-6-chloroquinolin-2-on-1-yl)benzamide 3-(Isoxazolo[3,4-c]-1,2-dihydro-3-methyl-6-chloroquinolin-2-on-1-yl)benzoyl chloride (50 mg, 0.134 mmol) and 3,4,5-trimethoxybenzyl amine (26.4 mg, 0.134 mmol) were converted to 76 mg of the title compound by the procedure of Example 30. (>100'). MS(FD) 533 (M+). IR υ3355, 2960, 2931, 1728, 1696, 1653, 1596 cm$^{-1}$.

Example 32

3-(Isoxazolo[3,4-c]-1,2-Dihydro-3-methyl-6-chloroquinolin-2-on-1-yl)phenylacetic Acid To a solution containing 4.50 g (11.2 mmol) of the compound of Prep 13 in 30 mL of dimethylformamide was added 20 mL of 2N sodium hydroxide in methanol. The reaction was stirred at room temperature for 2 hours and then diluted with 200 mL of ethyl acetate. This organic solution was washed with 1N aqueous hydrochloric acid (twice), brine (thrice), saturated aqueous sodium bicarbonate solution (twice), and concentrated to give an oily yellow solid. This crude material was purified by recrystallization to give 2.20 g (53%) of the title compound as a white crystalline solid. MS(FD) m/z 368 (M+).

Example 33

N-Phenyl-3-(Isoxazolo[3,4-c]-1,2-Dihydro-3-methyl-6-chloroquinolin-2-on-1-yl)phenylacetamide To a solution containing 3-(isoxazolo[3,4-c]-1,2-dihydro-3-methyl-6-chloroquinolin-2-on-1-yl)phenylacetyl chloride (65 mg, 0.167 mmol) in 1 mL of dichloromethane was added 30 μL (0.334 mmol) of aniline at room temperature. The reaction was stirred at room temperature for 10 minutes and then diluted with 20 mL of ethyl acetate. This organic solution was washed twice with 1N aqueous hydrochloric acid, dried over sodium sulfate, filtered, and concentrated in vacuo to give 60 mg (81%) of the title compound as a white solid. MS(FD) m/z 443 (M+).

Example 34

N-Benzyl-3-(Isoxazolo[3,4-c]-1,2-Dihydro-3-methyl-6-chloroquinolin-2-on-1-yl)phenylacetamide Benzylamine (21 μL, 0.19 mmol) and 3-(isoxazolo[3,4-c]-1,2-dihydro-3-methyl-6-chloroquinolin-2-on-1-yl)phenylacetyl chloride (37 mg, 0.095 mmol) were converted to the title compound by the procedure of Example 33 to yield 31 mg (70%). MS(FD) m/z 457 (M+).

Example 35

N-(Pyridin-4-ylmethyl)-3-(Isoxazolo[3,4-c]-1,2-Dihydro-3-methyl-6-chloroquinolin-2-on-1-yl)phenylacetamide 4-(Aminomethyl)pyridine (34 μL, 0.36 mmol) and 3-(isoxazolo[3,4-c]-1,2-dihydro-3-methyl-6- then concentrated in vacuo. No further purification was performed. MS(FD) m/z 498 (M+of free base). IR(KBr) υ 1674, 1597, 1475, 1197 cm$^{-1}$.

chloroquinolin-2-on-1-yl)phenylacetyl chloride (65 mg, 0.18 mmol) were converted to the title compound by the procedure of Example 33. MS(FD) m/z 458 (M+).

Example 36

N-(Pyridin-2-ylmethyl)-3-(Isoxazolo[3,4-c]-1,2-Dihydro-3-methyl-6-chloroquinolin-2-on-1-yl) phenylacetamide 2-(Aminomethyl)pyridine (34 μL, 0.36 mmol) and 3-(isoxazolo[3,4-c]-1,2-dihydro-3-methyl-6-chloroquinolin-2-on-1-yl)phenylacetyl chloride (65 mg, 0.18 mmol) were converted to the title compound by the procedure of Example 33. MS(FD) m/z 458 (M+).

Example 37

N-3,4,5-Trimethoxybenzyl-3-(Isoxazolo[3,4-c]-1,2-Dihydro-3-methyl-6-chloroquinolin-2-on-1-yl) phenylacetamide 3-(Isoxazolo[3,4-c]-1,2-dihydro-3-methyl-6-chloroquinolin-2-on-1-yl)phenylacetyl chloride (50 mg, 0.129 mmol) was dissolved in 2 mL of dry dichloromethane and stirred under nitrogen at room temperature. 3,4,5-Trimethoxybenzyl amine (28 mg, 0.142 mmol) was added followed by 21 μL of triethylamine. The reaction was stirred for about 18 hours and then diluted with ethyl acetate. The resulting mixture was washed three times each with 1N aqueous hydrochloric acid, aqueous sodium bicarbonate, and brine, dried over sodium sulfate, filtered, and concentrated. The residue was treated with methlyene chloride:hexanes to precipitate 57 mg of the title compound. (80%). MS(IS) 548 (M+). IR υ 3287, 1689, 1643, 1595, 1507.

Example 38

N,N-Dimethyl-3-(Isoxazolo[3,4-c]-1,2-Dihydro-3-methyl-6-chloroquinolin-2-on-1-yl)phenylacetamide 3-(Isoxazolo[3,4-c]-1,2-dihydro-3-methyl-6-chloroquinolin-2-on-1-yl)phenylacetyl chloride (50 mg, 0.129 mmol) and dimethylamine (6.4 mg, 0.142 mmol) were converted to 40 mg of the title compound by the procedure of Example 37. (78%). MS(IS) 396 (M+). IR(KBr) υ 1688, 1634, 1595.

Example 39

N-Methyl-3-(Isoxazolo[3,4-c]-1,2-Dihydro-3-methyl-6-chloroquinolin-2-on-1-yl)phenylacetamide 3-(Isoxazolo[3,4-c]-1,2-dihydro-3-methyl-6-chloroquinolin-2-on-1-yl)phenylacetyl chloride (50 mg, 0.129 mmol) and methylamine (4.4 mg, 0.142 mmol) were converted to 28 mg of the title compound by the procedure of Example 37. (57%). MS(IS) 382 (MS+). IR(CHCl₃) υ 3011, 1675, 1632, 1597.

Example 40

N-Methyl-3-(Isoxazolo[3,4-c]-1,2-Dihydro-3-methyl-6-chloroquinolin-2-on-1-yl)phenylacetamide Piperidinylmethylpolystyrene resin (72 mg) was placed in a screw top and bottom (with bottom frit) vial. Aminomethylcyclohexane (22 mg, 0.194 mmol) was then added followed by 2 mL of dry dichloromethane. 3-(Isoxazolo[3,4-c]-1,2-dihydro-3-methyl-6-chloroquinolin-2-on-1-yl)phenylacetyl chloride (50 mg, 0.129 mmol) was then added and the reaction was shaken for about 18 hours. Isocyanatylmethylpolystyrene resin (103 mg) was added and the vial was shaken again for four hours. The reaction was filtered and the resin was washed twice with methanol and dichloromethane. The solvents were removed in vacuo to give 37 mg of the title compound. (62%). MS(FD) 463 (M+). IR(CHCl₃) 3010, 2927, 1675, 1632, 1597 cm⁻¹.

Example 41

N-3,4,5-Trimethoxyphenyl-3-(Isoxazolo[3,4-c]-1,2-Dihydro-3-methyl-6-chloroquinolin-2-on-1-yl) phenylacetamide 3-(Isoxazolo[3,4-c]-1,2-dihydro-3-methyl-6-chloroquinolin-2-on-1-yl)phenylacetyl chloride (750 mg, 2.03 mmol) was dissolved in 60 mL dry dichloromethane and stirred under nitrogen at room temperature. Dimethylaminopyridine (25 mg, 0.203 mmol) and 1-ethyl-3-[3-(dimethylamino)propyl]carbodiimide hydrochloride (585 mg, 3.05 mmol) were then added. After stirring for about 15 minutes, 3,4,5-trimethoxyaniline (745 mg, 4.07 mmol) was added and the resulting mixture was stirred for about 18 hours. The reaction was diluted with ethyl acetate and this mixture was washed three times each with 1N aqueous hydrochloric acid, saturated aqueous sodium bicarbonate, and brine. The organics were dried over sodium sulfate, filtered, and evaporated. The residue was recrystallized from dichloromethane to give 851 mg of the title compound. (78%). MS(FD) 534 (M+). EA calculated for $C_{28}H_{24}N_3O_6Cl$: C, 62.98; H, 4.53; N, 7.87. Found: C, 62.81; H, 4.63; N, 7.72.

Example 42

N-4-Fluorophenyl-3-(Isoxazolo[3,4-c]-1,2-Dihydro-3-methyl-6-chloroquinolin-2-on-1-yl) phenylacetamide 3-(Isoxazolo[3,4-c]-1,2-dihydro-3-methyl-6-chloroquinolin-2-on-1-yl)phenylacetyl (50 mg, 0.136 mmol) and 4-fluoroaniline (25.7 μL, 0.272 mmol) were converted to 57 mg of the title compound by the procedure of Example 41. (90%).

Example 43

N-2,3,4,5,6-Pentafluorophenyl-3-(Isoxazolo[3,4-c]-1,2-Dihydro-3-methyl-6-chloroquinolin-2-on-1-yl) phenylacetamide 3-(Isoxazolo[3,4-c]-1,2-dihydro-3-methyl-6-chloroquinolin-2-on-1-yl)phenylacetic acid (50 mg, 0.136 mmol) and 2,3,4,5,6-pentafluoroaniline (50 mg, 0.272 mmol) were converted to 51 mg of the title compound by the procedure of Example 41. (71%). ¹H NMR consistent with desired product. MS(IS) 534 (M+).

Example 44

N-4-Trifluoromethoxyphenyl-3-(Isoxazolo[3,4-c]-1,2-Dihydro-3-methyl-6-chloroquinolin-2-on-1-yl) phenylacetamide 3-(Isoxazolo[3,4-c]-1,2-dihydro-3-methyl-6-chloroquinolin-2-on-1-yl)phenylacetic acid (50 mg, 0.136 mmol) and 4-trifluoromethoxyaniline (37 μL, 0.272 mmol) were converted to 64 mg of the title compound by the procedure of Example 41. (89%). ¹H NMR consistent with desired product. MS(IS) 528 (M+).

Example 45

N-3,4-Dimethoxyphenyl-3-(Isoxazolo[3,4-c]-1,2-Dihydro-3-methyl-6-chloroquinolin-2-on-1-yl)phenylacetamide 3-(Isoxazolo[3,4-c]-1,2-dihydro-3-methyl-6-chloroquinolin-2-on-1-yl)phenylacetic acid (50 mg, 0.136 mmol) and 4-trifluoromethoxyaniline (42 mg, 0.272 mmol) were converted to 57 mg of the title compound by the procedure of Example 41. (84%). MS(IS) 504 (M+). UV 316 (4576), 243 (36091), 219 (48616).

Example 46

N-1,3-Benzodioxol-6-yl-3-(Isoxazolo[3,4-c]-1,2-Dihydro-3-methyl-6-chloroquinolin-2-on-1-yl)phenylacetamide 3-(Isoxazolo[3,4-c]-1,2-dihydro-3-methyl-6-chloroquinolin-2-on-1-yl)phenylacetic acid (50 mg, 0.136 mmol) and 3,4-methylenedioxyaniline (37 mg, 0.272 mmol) were converted to 51 mg of the title compound by the procedure of Example 41. (77%). MS(IS) 488 (M+). IR 1684, 1632, 1596, 1567 cm$^{-1}$.

Example 47

N-4-Nitrophenyl-3-(Isoxazolo[3,4-c]-1,2-Dihydro-3-methyl-6-chloroquinolin-2-on-1-yl)phenylacetamide 3-(Isoxazolo[3,4-c]-1,2-dihydro-3-methyl-6-chloroquinolin-2-on-1-yl)phenylacetic acid (50 mg, 0.136 mmol) and 4-nitroaniline (37 mg, 0.272 mmol) were converted to 98 mg of the title compound by the procedure of Example 41. (>100%). MS(IS) 489 (M+). $^1$H NMR consistent with title compound.

Example 48

N-4-Methylphenyl-3-(Isoxazolo[3,4-c]-1,2-Dihydro-3-methyl-6-chloroquinolin-2-on-1-yl)phenylacetamide 3-(Isoxazolo[3,4-c]-1,2-dihydro-3-methyl-6-chloroquinolin-2-on-1-yl)phenylacetic acid (50 mg, 0.136 mmol) and 4-methylaniline (29 mg, 0.272 mmol) were converted to 57 mg of the title compound by the procedure of Example 41. (92%). MS (IS) 458 (M+). $^1$H NMR consistent with title compound.

Example 49

N-4-Trifluoromethylphenyl-3-(Isoxazolo[3,4-c]-1,2-Dihydro-3-methyl-6-chloroquinolin-2-on-1-yl)phenylacetamide 3-(Isoxazolo[3,4-c]-1,2-dihydro-3-methyl-6-chloroquinolin-2-on-1-yl)phenylacetic acid (50 mg, 0.136 mmol) and 4-trifluoromethylaniline (54 mg, 0.272 mmol) were converted to 47 mg of the title compound by the procedure of Example 41. (68%). MS(IS) 512 (M+). IR 3467, 3358, 3060, 2957, 2926, 1686, 1631, 1596 cm$^{-1}$.

Example 50

N-4-Methoxyphenyl-3-(Isoxazolo[3,4-c]-1,2-Dihydro-3-methyl-6-chloroquinolin-2-on-1-yl)phenylacetamide 3-(Isoxazolo[3,4-c]-1,2-dihydro-3-methyl-6-chloroquinolin-2-on-1-yl)phenylacetic acid (50 mg, 0.136 mmol) and 4-methoxyaniline (34 mg, 0.272 mmol) were converted to 51 mg of the title compound by the procedure of Example 41. (80%). MS(IS) 474 (M+). UV 315 (447), 242 (36450), 223 (45246).

Example 51

N-4-Carbomethoxyphenyl-3-(Isoxazolo[3,4-c]-1,2-Dihydro-3-methyl-6-chloroquinolin-2-on-1-yl)phenylacetamide 3-(Isoxazolo[3,4-c]-1,2-dihydro-3-methyl-6-chloroquinolin-2-on-1-yl)phenylacetic acid (50 mg, 0.136 mmol) and 4-carbomethoxyaniline (41 mg, 0.272 mmol) were converted to 55 mg of the title compound by the procedure of Example 41. (81%). MS(IS) 502 (M+). UV 270 (12189), 221 (39859).

Example 52

1-(N-t-Butyloxycarbonyl-3-(Isoxazolo[3,4-c]-1,2-Dihydro-3-methyl-6-chloroquinolin-2-on-1-yl)-α-Methylbenzylamine To a solution of N-(t-butyloxycarbonyl)-N'-(5-methyl-3-(2-chloro-6-fluorophenylisoxaz-4-oyl)-3-amino-α-methylbenzylamine (3.19 g, 6.74 mmol) in dry dimethylformamide (50 mL) was added a solution of sodium hydroxide (0.81 g, 20.2 mmol) in methanol. After overnight stirring at room temperature, the reaction mixture was poured onto ice, the solid was removed by vacuum filtration, and purified by liquid chromatography (10% ethyl acetate/hexanes) to afford 1.52 g of the title compound. (50% over 4 steps). MS(FAB) 454.2 (M+1). $^1$H NMR (CDCl$_3$): δ 1.38–1.44 (9H, m), 1.45–1.5 (3H, m), 2.9 (3H, s), 4.8–4.95 (2H, bs), 6.48–6.6 (1H, m), 7.1–7.63 (6H, m).

General Procedure for the Preparation of Examples 53–82

To individual solutions of commercially available amines (0.0851 mmol, 1.5 eq.) in dichloroethane (150 μL) in 1 ml glass vials was added a solution of 3-(isoxazolo[3,4-c]-1,2-dihydro-3-methyl-6-chloroquinolin-2-on-1-yl)acetophenone (0.0567 mmol, 1 eq.) in dichloroethane (150 μL). Triethylamine (0.0964 mmol, 1.7 equivalents per equivalent of hydrochloric acid where the amine employed existed as its hydrochloride salt) in dichloroethane (50 mL) was added to wells containing the amines. Each well was flushed with nitrogen followed by the addition of titanium (IV) isopropoxide (120 μL, 0.397 mmol). Each well was again flushed with nitrogen, capped, and then vortexed for 7–10 hours. To each well was added sodium cyanoborohydride (300 μL, 2.84 M in ethanol or methanol). The wells were flushed with nitrogen, capped, and then vortexed for 12 to 48 hours. The title compounds were isolated by prep TLC of the crude reaction mixtures. Hexane:ethyl acetate or methanol:chloroform solvent systems were employed. The yields ranged between 44 and 80% (25 to 46 mmol).

Example 53

α-Methyl-N-(Pyridin-2-ylmethyl)-3-(Isoxazolo[3,4-c]-1,2-Dihydro-3-methyl-6-chloroquinolin-2-on-1-yl)benzylamine MS(IS) 444.9 (M+). $^1$H NMR(CDCl$_3$) δ 8.54 (d, 1H, J=5 Hz), 7.65–7.52 (m, 3H), 7.38–7.11 (m, 6H), 6.60–6.50 (m, 1H), 3.99–3.85 (m, 1H), 3.83 (s, 2H), 2.92 (s, 3H), 1.47 (d, 3H, J 6 Hz).

Example 54

α-Methyl-N-(4-Dimethylaminobenzyl)-3-(Isoxazolo[3,4-c]-1,2-Dihydro-3-methyl-6-chloroquinolin-2-on-1-yl)benzylamine MS(IS) 487.5 (M+). $^1$H NMR (CDCl$_3$) δ 7.63–7.57 (m, 2H), 7.38–7.10 (m, 6H), 6.70–6.50 (m, 3H), 3.98–3.88 (m, 1H), 2.70–3.51 (m, 2H), 2.94–2.91 (mn, 9H), 1.43 (d, 3H, J=6 Hz).

Example 55

α-Methyl-N-(Carboethoxymethyl)-3-(Isoxazolo[3,4-c]-1,2-Dihydro-3-methyl-6-chloroquinolin-2-on-1-yl)benzylamine

MS(IS) 439.9 (M+).

Example 56

N-[α-Methyl-3-(Isoxazolo[3,4-c]-1,2-Dihydro-3-methyl-6-chloroquinolin-2-on-1-yl)benzyl]morpholine

MS(IS) 423.9 (M+).

Example 57

α-Methyl-N-(2-Piperidinylethyl)-3-(Isoxazolo[3,4-c]-1,2-Dihydro-3-methyl-6-chloroquinolin-2-on-1-yl)benzylamine

MS(IS) 450.8 (M+).

Example 58

α-Methyl-N-(Furan-2-ylmethyl)-3-(Isoxazolo[3,4-c]-1,2-Dihydro-3-methyl-6-chloroquinolin-2-on-1-yl)benzylamine

MS(IS) 433.9 (M+).

Example 59

α-Methyl-N-(2-Methoxyethyl)-3-(Isoxazolo[3,4-c]-1,2-Dihydro-3-methyl-6-chloroquinolin-2-on-1-yl)benzylamine

MS(IS) 411.9 (M+).

Example 60

α-Methyl-N-(Benzyl)-3-(Isoxazolo[3,4-c]-1,2-Dihydro-3-methyl-6-chloroquinolin-2-on-1-yl)benzylamine

MS(IS) 443.9 (M+).

Example 61

α-Methyl-N-(3,5-Dimethoxybenzyl)-3-(Isoxazolo[3,4-c]-1,2-Dihydro-3-methyl-6-chloroquinolin-2-on-1-yl)benzylamine

MS(IS) 503.9 (M+).

Example 62

α-Methyl-N-(Tetrahydrofuran-2-ylmethyl)-3-(Isoxazolo[3,4-c]-1,2-Dihydro-3-methyl-6-chloroquinolin-2-on-1-yl)benzylamine

MS(IS) 437.8 (M+).

Example 63

α-Methyl-N-(3-Pyrolidin-2-onylpropyl)-3-(Isoxazolo[3,4-c]-1,2-Dihydro-3-methyl-6-chloroquinolin-2-on-1-yl)benzylamine

MS(IS) 478.8 (M+).

Example 64

α-Methyl-N-(2-Acetamidylethyl)-3-(Isoxazolo[3,4-c]-1,2-Dihydro-3-methyl-6-chloroquinolin-2-on-1-yl)benzylamine

MS(IS) 439.5 (M+).

Example 65

α-Methyl-N-(Cyclohexyl)-3-(Isoxazolo[3,4-c]-1,2-Dihydro-3-methyl-6-chloroquinolin-2-on-1-yl)benzylamine

MS(IS) 439.9 (M+).

Example 66

α-Methyl-N-(Isopropyl)-3-(Isoxazolo[3,4-c]-1,2-Dihydro-3-methyl-6-chloroquinolin-2-on-1-yl)benzylamine

MS(IS) 396.4 (M+).

Example 67

α-Methyl-N-(2,6-Dimethoxybenzyl)-3-(Isoxazolo[3,4-c]-1,2-Dihydro-3-methyl-6-chloroquinolin-2-on-1-yl)benzylamine

MS(IS) 504.4 (M+).

Example 68

α-Methyl-N-(4-Trifluoromethylbenzyl)-3-(Isoxazolo[3,4-c]-1,2-Dihydro-3-methyl-6-chloroquinolin-2-on-1-yl)benzylamine

MS(IS) 512.5 (M+).

Example 69

α-Methyl-N-(1-Methyl-2-Carboisopropoxyethyl)-3-(Isoxazolo[3,4-c]-1,2-Dihydro-3-methyl-6-chloroquinolin-2-on-1-yl)benzylamine

MS(IS) 482.5 (M+).

Example 70

α-Methyl-N-(1-Carboisopropoxy-2-[4-Trifluoromethylphenyle]thyl)-3-(Isoxazolo(3,4-c]-1,2-Dihydro-3-methyl-6-chloroquinolin-2-on-1-yl)benzylamine

MS(IS) 544.5 (M+).

Example 71

α-Methyl-N-(1-Carboisopropoxy-2-Methylpropyl)-3-(Isoxazolo[3,4-c]-1,2-Dihydro-3-methyl-6-chloroquinolin-2-on-1-yl)benzylamine

MS(IS) 496.6 (M+).

Example 72

α-Methyl-N-(1-Carboisopropoxy-2-[Indol-3-yl]ethyl)-3-(Isoxazolo[3,4-c]-1,2-Dihydro-3-methyl-6-chloroquinolin-2-on-1-yl)benzylamine

MS(IS) 544.5 (M+).

Example 73

α-Methyl-N-(1,2-Bis-Carboisopropoxyethyl)-3-(Isoxazolo[3,4-c]-1,2-Dihydro-3-methyl-6-chloroquinolin-2-on-1-yl)benzylamine

MS(IS) 554.5 (M+).

Example 74

1-(1-[R-2-Carboisopropoxy]pyrrolidinyl)ethyl-3-(Isoxazolo[3,4-c]-1,2-Dihydro-3-methyl-6-chloroquinolin-2-on-1-yl)benzene

MS(IS) 494.7 (M+).

Example 75

α-Methyl-N-(4-Sulfonaminylbenzyl)-3-(Isoxazolo[3,4-c]-1,2-Dihydro-3-methyl-6-chloroquinolin-2-on-1-yl)benzylamine

MS(IS) 523.5 (M+).

Example 76

α-Methyl-N-(1-Carboisopropoxy-3-Methylthiopropyl)-3-(Isoxazolo[3,4-c]-1,2-Dihydro-3-methyl-6-chloroquinolin-2-on-1-yl)benzylamine

MS(IS) 528.4 (M+).

Example 77

α-Methyl-N-Carboxymethyl-3-(Isoxazolo[3,4-c]-1,2-Dihydro-3-methyl-6-chloroquinolin-2-on-1-yl)benzylamine Hydrochloride

MS(IS) 412.5 (M+).

Example 78

α-Methyl-N-(1-Methyl-2-Carboxyethyl)-3-(Isoxazolo[3,4-c]-1,2-Dihydro-3-methyl-6-chloroquinolin-2-on-1-yl)benzylamine Hydrochloride

MS(IS) 440.6 (M+).

Example 79

α-Methyl-N-(1-Carboxy-2-[Indol-3-yl]ethyl)-3-(Isoxazolo[3,4-c]-1,2-Dihydro-3-methyl-6-chloroquinolin-2-on-1-yl)benzylamine Hydrochloride

MS(IS) 541.5 (M+).

Example 80

α-Methyl-N-(1-Carboxy-2-Methylpropyl)-3-(Isoxazolo[3,4-c]-1,2-Dihydro-3-methyl-6-chloroquinolin-2-on-1-yl)benzylamine Hydrochloride

MS(IS) 454.3 (M+).

Example 81

α-Methyl-N-(1,3-Biscarboxyethyl)-3-(Isoxazolo[3,4-c]-1,2-Dihydro-3-methyl-6-chloroquinolin-2-on-1-yl)benzylamine Hydrochloride

MS(IS) 484.3 (M+).

Example 82

1-(1-[R-2-Carboxy]pyrrolidinyl)ethyl-3-(Isoxazolo[3,4-c]-1,2-Dihydro-3-methyl-6-chloroquinolin-2-on-1-yl)benzene Hydrochloride

MS(IS) 452.2 (M+).

General Procedure for the Combinatorial Preparation of Examples 83–119

To a solution of 3-(isoxazolo[3,4-c]1,2-dihydro-3-methyl-6-chloroquinolin-2-on-1-yl)aniline or 3-(isoxazolo[3,4-c]-1,2-dihydro-3-methyl-6-chloroquinolin-2-on-1-yl) benzylamine (0.0809 mmol) in dichloromethane (0.5 mL) was added triethylamine (0.0327 g, 0.324 mmol) followed by a 1M solution of a commercially available acid chloride, isocyanate, or isothiocyanate (0.08899 mmol). After stirring 24 hours at room temperature, the reaction mixture in each well was washed with excess aminomethylpolystyrene resin. The solvent in each well was removed under reduced pressure and the resulting residue was resuspended in dichloromethane (0.5 ml). The suspension was washed with 1M aqueous hydrochloric acid (0.4 ml), the aqueous layer was removed, and the organic solvent evaporated to provide the title compound.

Example 83

N-(Benzoyl)-3-(Isoxazolo[3,4-c]-1,2-Dihydro-3-methyl-6-chloroquinolin-2-on-1-yl)aniline

Example 84

N-(Cyclohexanoyl)-3-(Isoxazolo[3,4-c]-1,2-Dihydro-3-methyl-6-chloroquinolin-2-on-1-yl)aniline

Example 85

N-(Quinoxalin-2-oyl)-3-(Isoxazolo[3,4-c]-1,2-Dihydro-3-methyl-6-chloroquinolin-2-on-1-yl)aniline

Example 86

N-(1-Benzyl-3-t-Butylpyrazol-5-oyl)-3-(Isoxazolo[3,4-c]-1,2-Dihydro-3-methyl-6-chloroquinolin-2-on-1-yl)aniline

Example 87

N-(5-Methylisoxazol-3-oyl)-3-1-3-(Ioxazlo[3,4-c]-1,2-Dihydro-3-methyl-6-chloroquinolin-2-on-1-yl)aniline

Example 88

N-(Indol-3-oyl)-3-(Isoxazolo[3,4-c]-1,2-Dihydro-3-methyl-6-chlorquinolin-2-on-1-yl)aniline

Example 89

N-(Morpholin oyl)-3-(Isoxazolo[3,4-c]-1,2-Dihydro-3-methyl-6-chloroquinolin-2-on-1-yl)aniline

Example 90

N-(3,5-Dimethylisoxazol-4-oyl)-3-(Isoxazolo[3,4-c]-1,2-Dihydro-3-methyl-6-chloroquinolin-2-on-1-yl)aniline

Example 91

N-(2-Piperidinylpropanoyl)-3-(Isoxazolo[3,4-c]-1,2-Dihydo-3-methyl-6-chloroquinolin-2-on-1-yl)aniline

Example 92

N-(-Phenyl-5-Trifluoromethylpyrazol-4-oyl)-3-(Isoxazolo[3,4-c]-1,2-Dihydro-3-methyl-6-chloroquinolin-2-on-1-yl)aniline

Example 93

N-(1-Methyl-3-t-Butylpyrazol-5-oyl)-3-(Isoxazolo[3,4-c]-1,2-Dihydro-3-methyl-6-chloroquinolin-2-on-1-yl)aniline

Example 94

N-(1,4-Benzodioxan-2-oyl)-3-(Isoxazolo[3,4-c]-1,2-Dihydro-3-methyl-6-chloroquinolin-2-on-1-yl)aniline

Example 95

N-(Benzoyl)-3-(Isoxazolo[3,4-c]-1,2-Dihydro-3-methyl-6-chloroquinolin-2-on-1-yl)benzylamine

Example 96

N-(Cyclohexanoyl)-3-(Isoxazolo[3,4-c]-1,2-Dihydro-3-methyl-6-chloroquinolin-2-on-1-yl)benzylamine

Example 97

N-(Quinoxalin-2-oyl)-3-(Isoxazolo[3,4-c]-1,2-Dihydro-3-methyl-6-chloroquinolin-2-on-1-yl)benzylamine

Example 98

N-(1-Benzyl-3-t-Butylpyrazol-5-oyl)-3-(Isoxazolo[3,4-c]-1,2-Dihydro-3-methyl-6-chloroquinolin-2-on-1-yl)benzylamine

Example 99

N-(5-Methylisoxazol-3-oyl)-3-(Isoxazolo[3,4-c]-1,2-Dihydro-3-methyl-6-chloroquinolin-2-on-1-yl)benzylamine

Example 100

N-(Indol-3-oyl)-3-(Isoxazolo[3,4-c]-1,2-Dihydro-3-methyl-6-chloroquinolin-2-on-1-yl)benzylamine

Example 101

N-(Morpholinoyl)-3-(Isoxazolo[3,4-c]-1,2-Dihydro-3-methyl-6-chloroquinolin-2-on-1-yl)benzylamine

Example 102

N-(3,5-Dimethylisoxazol-4-oyl)-3-(Isoxazolo[3,4-c]-1,2-Dihydro-3-methyl-6-chloroquinolin-2-on-1-yl)benzylamine

Example 103

N-(2-Piperidinylpropanoyl)-3-(Isoxazolo[3,4-c]-1,2-Dihydro-3-methyl-6-chloroquinolin-2-on-1-yl)benzylamine

Example 104

N-(1-Phenyl-5-Trifluoromethylpyrazol-4-oyl)-3-(Isoxazolo[3,4-c]-1,2-Dihydro-3-methyl-6-chloroquinolin-2-on-1-yl)benzylamine

Example 105

N-(1-Methyl-3-t-Butylpyrazol-5-oyl)-3-(Isoxazolo[3,4-c]-1,2-Dihydro-3-methyl-6-chloroquinolin-2-on-1-yl)benzylamine.

Example 106

N-(1,4-Benzodioxan-2-oyl)-3-(Isoxazolo[3,4-c]-1,2-Dihydro-3-methyl-6-chloroquinolin-2-on-1-yl)benzylamine

Example 107

N-(3,4,5-Trimethoxybenzoyl)-3-(Isoxazolo[3,4-c]-1,2-Dihydro-3-methyl-6-chloroquinolin-2-on-1-yl)benzylamine

Example 108

N-(2-Methylbenzoyl)-3-(Isoxazolo[3,4-c]-1,2-Dihydro-3-methyl-6-chloroquinolin-2-on-1-yl)benzylamine

Example 109

N-(2-Chlorothiophen-5-oyl)-3-(Isoxazolo[3,4-c]-1,2-Dihydro-3-methyl-6-chloroquinolin-2-on-1-yl) benzylamine

Example 110

N-(1-Phenylpyrazol-4-oyl)-3-(Isoxazolo[3,4-c]-1,2-Dihydro-3-methyl-6-chloroquinolin-2-on-1-yl) benzylamine

Example 111

N-(1-[4-Chlorophenyl]cyclopentanoyl)-3-(Isoxazolo[3,4-c]-1,2-Dihydro-3-methyl-6-chloroquinolin-2-on-1-yl)benzylamine

Example 112

N-(1-Oxo-3-[Benzoxazin-4-on-1-yl]propyl)-3-(Isoxazolo[3,4-c]-1,2-Dihydro-3-methyl-6-chloroquinolin-2-on-1-yl) benzylamine

Example 113

N-(n-Pentanesulfonyl)-3-(Isoxazolo[3,4-c]-1,2-Dihydro-3-methyl-6-chloroquinolin-2-on-1-yl) benzylamine

Example 114

N-(4-Methylbenzenesulfonyl)-3-(Isoxazolo[3,4-c]-1,2-Dihydro-3-methyl-6-chloroquinolin-2-on-1-yl) benzylamine

Example 115

N-(4-t-Butylbenzenesulfonyl)-3-(Isoxazolo[3,4-c]-1,2-Dihydro-3-methyl-6-chloroquinolin-2-on-1-yl) benzylamine

Example 116

N-(4-Methylphenyl)-N'-3-([Isoxazolo[3,4-c]-1,2-Dihydro-3-methyl-6-chloroquinolin-2-on-1-yl] benzyl) Urea

Example 117

N-(3,5-Ditrifluoromethylphenyl)-N'-(3-[Isoxazolo[3,4-c]-1,2-Dihydro-3-methyl-6-chloroquinolin-2-on-1-yl]benzyl) Urea

Example 118

N-(4-Chlorophenyl)-N'-(3-[Isoxazolo[3,4-c]-1,2-Dihydro-3-methyl-6-chloroquinolin-2-on-1-yl]benzyl) Urea

Example 119

N-(3,5-Ditrifluoromethylphenyl)-N'-(3-[Isoxazolo[3,4-c]-1,2-Dihydro-3-methyl-6-chloroquinolin-2-on-1-yl]benzyl) Thiourea General Procedure for the Combinatorial Preparation of Examples 120–137

To a solution of 3-(Isoxazolo[2,4-c]1,2-dihydro-3-methyl-6-chloroquinolin-2-on-1-yl) aniline or 3-(isoxazolo[3,4-c]-1,2-dihydro-3-methyl-6-chloroquinolin-2-on-1-yl) benzylamine (0.0386 mmol) in 2:1 1,2-dichloroethane:methanol (0.5 mL) was added a 1M solution of commercially available aldehyde (0.0425 mmol) and sodium triacetoxyborohydride (0.025 g, 0.116 mmol) in acetic acid (0.05 mL). After stirring for 24 hours at room temperature, the reaction mixture in each well of the plate was filtered through a cellulose frit and the solvent was removed under reduced pressure. The residue in each well was then suspended in dichloromethane (0.5 mL), washed with water (0.4 mL) and the solvent again removed under vacuum. The reaction mixtures were redissolved in dichloromethane (0.5 mL) and stirred in excess aminomethylpolystyrene resin overnight. The next day, the contents of each well were individually filtered through a cellulose frit, and the solvent evaporated to provide the title compound.

Example 120

N-(Pyridin-4-ylmethyl)-3-(Isoxazolo[3,4-c]-1,2-Dihydro-3-methyl-6- chloroquinolin-2-on-1-yl) aniline

Example 121

N-(4-Methylthiobutyl)-3-(Isoxazolo[3,4-c]-1,2-Dihydro-3-methyl-6-chloroquinolin-2-on-1-yl) aniline

Example 122

N-(2-Carboethoxycyclopropylmethyl)-3-(Isoxazolo[3,4-c]-1,2-Dihydro-3-methyl-6-chloroquinolin-2-on-1-yl)aniline

Example 123

N-(Phenylethyl)-3-(Isoxazolo[3,4-c]-1,2-Dihydro-3-methyl-6-chloroquinolin-2-on-1-yl)aniline

Example 124

N-(4-Trifluoromethylbenzyl)-3-(Isoxazolo[3,4-c]-1,2-Dihydro-3-methyl-6-chloroquinolin-2-on-1-yl) aniline

Example 125

N-(4-Hydroxybenzyl)-3-(Isoxazolo[3,4-c]-1,2-Dihydro-3-methyl-6-chloroquinolin-2-on-1-yl) aniline

Example 126

N-(4-Dimethylaminobenzyl)-3-(Isoxazolo[3,4-c]-1, 2-Dihydro-3-methyl-6-chloroquinolin-2-on-1-yl) aniline

Example 127

N-(Piperonyl)-3-(Isoxazolo[3,4-c]-1,2-Dihydro-3-methyl-6-chloroquinolin-2-on-1-yl)aniline

Example 128

N-(2-Methylfuran-5-ylmethyl)-3-(Isoxazolo[3,4-c]-1,2-Dihydro-3-methyl-6-chloroquinolin-2-on-1-yl) aniline

Example 129

N-(3-Dimethlamino-2,2-Dimethylpropyl)-3-(Isoxazolo[3,4-c]-1,2-Dihydro-3-methyl-6-chloroquinolin-2-on-1-yl)aniline

Example 130

N-(1-Methylpyrrol-2-ylmethyl)-3-(Isoxazolo[3,4-c]-1,2-Dihydro-3-methyl-6-chloroquinolin-2-on-1-yl) aniline

Example 131

N-Benzoyl-3-(Isoxazolo[3,4-c]-1,2-Dihydro-3-methyl-6-chloroquinolin-2-on-1-yl) aniline

Example 132

N-(Indol-3-ylmethyl)-3-(Isoxazolo[3,4-c]-1,2-Dihydro-3-methyl-6-chloroquinolin-2-on-1-yl) aniline

Example 133

N-(3,5-Difluorobenzyl)-3-(Isoxazolo[3,4-c]-1,2-Dihydro-3-methyl-6-chloroquinolin-2-on-1-yl) aniline

Example 134

N-(2,6-Dimethoxybenzyl)-3-(Isoxazolo[3,4-c]-1,2-Dihydro-3-methyl-6-chloroquinolin-2-on-1-yl) aniline

Example 135

N-(Pyridin-4-ylmethyl)-3-(Isoxazolo[3,4-c]-1,2-Dihydro-3-methyl-6-chloroquinolin-2-on-1-yl) benzylamine

Example 136

N-(Methylthiobutyl)-3-(Isoxazolo[3,4-c]-1,2-Dihydro-3-methyl-6-chloroquinolin-2-on-1-yl) benzylamine

Example 137

N-(2-Carboethoxycyclopropylmethyl)-3-(Isoxazolo[3,4-c]-1,2-Dihydro-3-methyl-6-chloroquinoin-2-on-1-yl)benzylamine General Procedure f or the Combinatorial Preparation of Examples 138–147

Piperidinylmethylpolystyrene (72–144 mg, 2–4 equivalents) was placed in a top and bottom screw top (with bottom frit) vial. 1 mL of dry dichloromethane was added followed by 1.5 equivalents of a commercially available amine. 3-(Isoxazolo[3,4-c]-1,2-dihydro-3-methyl-6-chloroquinolin-2-on-1-yl)phenylacetyl chloride (50 mg, 0.129 mmol) in 5 mL of dichloromethane was added to each vial. The mixtures were shaken for about 18 hours. Isocyanatylmethylpolystyrene resin (193 mg) was then added (estimated for each vial) and shaken for 6 hours. Each vial was filtered into another vial and the resins washed twice each with 1 mL of methanol then 1 mL of dichloromethane. The solvents from the individually combined filtrates and washes for each well were removed (nitrogen blown over the top of the vial) to give the title compound.

Example 138

N-(Bicyclo[2.2.1]heptan-2-yl)-3-(Isoxazolo[3,4-c]-1, 2-Dihydro-3-methyl-6-chloroquinolin-2-on-1-yl) phenylacetamide MS(IS) 444.9. $^1$H NMR (CDCl$_3$) δ 8.54 (d, 1H, J=5 Hz), 7.65–7.52 (m, 3H), 7.38–7.11 (m, 6H), 6.60–6.50 (m, 1H), 3.99–3.85 (m, 1H), 3.83 (s, 2H), 2.92 (s, 3H), 1.47 (d, 3H, J=6 Hz)

Example 139

N-(2-Phenylpropyl)-3-(Isoxazolo[3,4-c]-1,2-Dihydro-3-methyl-6-chloroquinolin-2-on-1-yl) phenylacetamide MS(IS) 487.5 (M+). $^1$H NMR (CDCl$_3$) δ 7.63–7.57 (m, 2H), 7.38–7.10 (m, 6H), 6.70–6.50 (m, 3H), 3.98–3.88 (m, 1H), 3.70–3.51 (m, 2H), 2.94–2.91 (m, 9H), 1.43 (d, 3H, J=6 Hz).

Example 140

N-(Pyrazol-3-yl)-3-(Isoxazolo[3,4-c]-1,2-Dihydro-3-methyl-6-chloroquinolin-2-on-1-yl)phenylacetamide

MS(IS) 439.9 (M+).

Example 141

N-(1,3-Biscarbomethoxypropyl)-3-(Isoxazolo[3,4-c]-1,2-Dihydro-3-methyl-6-chloroquinolin-2-on-1-yl)phenylacetamide

MS(IS) 423.9 (M+).

Example 142

N-(3,5-Dimethoxybenzyl)-3-(Isoxazolo[3,4-c]-1,2-Dihydro-3-methyl-6-chloroquinolin-2-on-1-yl) phenylacetamide

MS(IS) 450.8 (M+).

Example 143

N-(4-Cyclohexylphenyl)-3-(Isoxazolo[3,4-c]-1,2-Dihydro-3-methyl-6-chloroquinolin-2-on-1-yl)phenylacetamide

MS(IS) 433.9 (M+).

Example 144

N-(2-Indol-3-ylethyl)-3-(Isoxazolo[3,4-c]-1,2-Dihydro-3-methyl-6-chloroquinolin-2-on-1-yl)phenylacetamide

MS(IS) 411.9 (M+).

Example 145

N-(N-t-Butyloxycarbonyl-Aminoethyl)-3-(Isoxazolo[3,4-c]-1,2-Dihydro-3-methyl-6-chloroquinolin-2-on-1-yl)phenylacetamide

MS(IS) 443.9 (M+).

Example 146

N-(Tetrahydrofuran-2-ylmethyl)-3-(Isoxazolo[3,4-c]-1,2-Dihydro-3-methyl-6-chloroquinolin-2-on-1-yl)phenylacetamide

MS(IS) 503.9 (M+).

Example 147

N-(Napth-2-yl)-3-(Isoxazolo[3,4-c]-1,2-Dihydro-3-methyl-6-chloroquinolin-2-on-1-yl)aniline

MS(IS) 437.8 (M+).

Example 148

1-(3-Aminobenzyl)-3-Isoxazolo[3,4-c]-1,2-Dihydro-3-Methyl-6-Chloroquinolin-2-one 1-(3-Nitrobenzyl)-3-isoxazolo[3,4-c]-1,2-dihydro-3-methyl-6-chloroquinolin-2-one (788 mg, 2.13 mmol) was converted to product by the procedure of Preparation 2. MS(IE) m/z 340 (M+1). IR 3300, 1683, 1632, 1608, 1462, 1318 cm$^{-1}$.

Example 149

1-(N-3,4,5-Trimethoxybenzoyl-3-Aminobenzyl)-3-Isoxazolo[3,4-c]-1,2-Dihydro-3-Methyl-6-Chloroquinolin-2-one 1-(3-Aminobenzyl)-3-isoxazolo[3,4-c]-1,2-dihydro-3-methyl-6-chloroquinolin-2-one (160 mg, 0.471 mmol) was dissolved in 10 mL of dimethylformamide and 3,4,5-trimethoxybenzoyl chloride (109 mg, 0.471 mmol) and triethylamine (79 mL, 0.565 mmol) were added. The resulting mixture was stirred at room temperature for 15 hours then diluted with ethyl acetate, washed three times with aqueous sodium hydroxide, 1N aqueous hydrochloric acid, dried over sodium sulfate, filtered, and concentrated in vacuo. The residue was recrystallized from methanol to give 85 mg of the title compound. MS(IE) m/z 534 (M+1). IR 3250, 1666, 1596, 1130 cm$^{-1}$.

Example 150

N-(4-Methanesulfonylbenzoyl)-3-(Isoxazolo[3,4-c]-1,2-Dihydro-3-methyl-6-chloroquinolin-2-on-1-yl)benzylamine 4-Sulfonamylbenoic acid (44 mg, 0.221 mmol) was dissolved in 3 mL of dry dimethylformamide and 2 mL of dry dichloromethane and stirred at room temperature under nitrogen. DMAP (3 mg, 0.022 mmol) and EDCI (63 mg, 0.331 mmol) were added and the reaction was stirred for 15 minutes. 3-(Isoxazolo[3,4-c]-1,2-dihydro-3-methyl-6-chloroquinolin-2-on-1-yl)benzylamine (75 mg, 0.221 mmol) was added and the resulting mixture was stirred for about 18 hours. The reaction was diluted with ethyl acetate and 1N aqueous hydrochloric acid. The ethyl acetate was separated, washed two more times with 1N hydrochloric acid (25 mL), sodium bicarbonate (3×25 mL), and brine (3×25 mL), dried over sodium sulfate, filtered, and concentrated. The residue was chromatographed (silica gel, ethyl acetate) to give 34.6 mg of the title compound. (63%). MS(FD) m/z 522 (M+). IR(KBr) 3371, 3311, 1680, 1658 cm$^{-1}$.

Example 151

N-(4-Dipropylaminosulfonylbenzoyl)-3-(Isoxazolo[3,4-c]-1,2-Dihydro-3-methyl-6-chloroquinolin-2-on-1-yl)benzylamine N,N'-Bis-n-propyl-4-sulfonamylbenzoic acid (63 mg, 0.221 mmol) and 3-(isoxazolo[3,4-c]-1,2-dihydro-3-methyl-6-chloroquinolin-2-on-1-yl)benzylamine (75 mg, 0.221 mmol) were converted to 123 mg of the title compound by the procedure of Example 150 except chromatographic purification of the product residue was not performed. (92%). EA calculated for $C_{31}H_{31}ClN_4O_5S$: C, 61.33; H, 5.15; N, 9.23. Found: C, 61.16; H, 5.07; N, 9.12. MS(FD) m/z 606 (M+).

Example 152

N-(3,4,5-Triethoxybenzoyl)-3-(Isoxazolo[3,4-c]-1,2-Dihydro-3-methyl-6-chloroquinolin-2-on-1-yl)benzylamine 3,4,5-Triethyoxybenzoic acid (37 mg, 0.147 mmol) and 3-5 (isoxazolo[3,4-c]-1,2-dihydro-3-methyl-6-chloroquinolin-2-on-1-yl)benzylamine (50 mg, 0.147 mmol) were converted to the title compound by the procedure of Example 150.

Example 153

N-(1-Oxo-3-(4-Aminosulfonylanilinyl)propyl)-3-(Isoxazolo[3,4-c]-1,2-Dihydro-3-methyl-6-chloroquinolin-2-on-1-yl)benzylamine 3-(4-Sulfonamylanilinyl)propanoic acid (54 mg, 0.221 mmol) and 3-(isoxazolo[3,4-c]-1,2-dihydro-3-methyl-6-chloroquinolin-2-on-1-yl)benzylamine (75 mg, 0.221 mmol) were converted to 106 mg of the title compound by the procedure of Example 150 except that instead of chromatographic purification, the residue was treated with dichloromethane and hexanes to precipitate the product. (85%). MS(FD) m/z 565 (M+). IR(KBr) 3381, 3291, 1688, 1651, 1631, 1597 cm$^{-1}$.

Example 154

N-6-Methoxyquinolin-8-yl-3-(Isoxazolo[3,4-c]-1,2-Dihydro-3-methyl-6-chloroquinolin-2-on-1-yl)phenylacetamide 3-(Isoxazolo[3,4-c]-1,2-dihydro-3-methyl-6-chloroquinolin-2-on-1-yl)phenylacetic acid (50 mg, 0.136 mmol) was dissolved in 2 mL of dry dimethylformamide and stirred at room temperature under nitrogen. DMAP (2 mg, 0.014 mmol), EDCI (39 mg, 0.203 mmol), and 6-methoxy-8-aminoquinoline (26 mg, 0.122 mmol) were added and the resulting mixture was stirred for about 18 hours. The reaction was diluted with ethyl acetate and washed with saturated aqueous sodium bicarbonate and brine and concentrated. The residue was chromatographed (silica gel, 1:1 ethyl acetate:hexanes) to give 21 mg of the title compound which was recrystallized from dichloromethane/hexanes. (63%). MS(IS) m/z 525.1 (M+). IR(KBr) 1683, 1628, 1596, 1528 cm$^{-1}$.

Example 155

N-(4-Aminosulfonylphenyl)-3-(Isoxazolo[3,4-c]-1,2-Dihydro-3-methyl-6-chloroquinolin-2-on-1-yl)phenylacetamide 3-(Isoxazolo[3,4-c]-1,2-dihydro-3-methyl-6-chloroquinolin-2-on-1-yl)phenylacetic acid (50 mg, 0.136 mmol) and 4-sulfonamylaniline (47 mg, 0.271 mmol) were converted to 50 mg the title compound by the procedure of Example 155. (70%). MS(FD) m/z 522 (M+). UV(ethanol) λ(ε) 315 (3688), 245 (38968), 22 (37669).

Example 156

N-(4-Aminosulfonylbenzyl)-3-(Isoxazolo[3,4-c]-1,2-Dihydro-3-methyl-6-chloroquinolin-2-on-1-yl)phenylacetamide 3-(Isoxazolo[3,4-c]-1,2-dihydro-3-methyl-6-chloroquinolin-2-on-1-yl)phenylacetic acid (50 mg, 0.136 mmol) and 4-sulfonamylbenzylamine hydrochloride (60 mg, 0.271 mmol) were converted to 62 mg the title compound by the procedure of Example 155 except that 1.1 equivalents of DMAP were employed. (84%). MS(FD) m/z 536 (M+). UV(ethanol) 316 (3164), 224 (46241).

Example 157

N-[2-methylphenyl]3-(Isoxazolo[3,4-c]-1,2-Dihydro-3-methyl-6-chloroquinolin-2-on-1-yl)phenylacetamide Beginning with 3-(Isoxazolo[3,4-c]-1,2-dihydro-3-methyl-6-chloroquinolin-2-on-1-yl)phenylacetyl chloride and 2-methylaniline, the title compound was prepared essentially as described in Example 41.

MS(IS) m/z 458 (M+1).

Example 158

N-[3-methylphenyl]3-(Isoxazolo[3,4-c]-1,2-Dihydro-3-methyl-6-chloroquinolin-2-on-1-yl)phenylacetamide Beginning with 3-(Isoxazolo[3,4-c]-1,2-dihydro-3-methyl-6-chloroquinolin-2-on-1-yl)phenylacetyl chloride and 3-methylaniline, the title compound was prepared essentially as described in Example 41.

MS(IS) m/z 458 (M+1).

Example 159

N-[2,3-dimethylphenyl]3-(Isoxazolo[3,4-c]-1,2-Dihydro-3-methyl-6-chloroquinolin-2-on-1-yl)phenylacetamide Beginning with 3-(Isoxazolo[3,4-c]-1,2-dihydro-3-methyl-6-chloroquinolin-2-on-1-yl)phenylacetyl chloride and 2,3-dimethylaniline, the title compound was prepared essentially as described in Example 41.

MS(IS) m/z 472 (M+1).

Example 160

N-[2,4-dimethylphenyl]3-(Isoxazolo[3,4-c]-1,2-Dihydro-3-methyl-6-chloroquinolin-2-on-1-yl)phenylacetamide Beginning with 3-(Isoxazolo[3,4-c]-1,2-dihydro-3-methyl-6-chloroquinolin-2-on-1-yl)phenylacetyl chloride and 2,4-dimethylaniline, the title compound was prepared essentially as described in Example 41.

MS(IS) m/z 472 (M+1).

Example 161

N-[2,5-dimethylphenyl]3-(Isoxazolo[3,4-c]-1,2-Dihydro-3-methyl-6-chloroquinolin-2-on-1-yl)phenylacetamide Beginning with 3-(Isoxazolo[3,4-c]-1,2-dihydro-3-methyl-6-chloroquinolin-2-on-1-yl)phenylacetyl chloride and 2,5-dimethylaniline, the title compound was prepared essentially as described in Example 41.

MS(IS) m/z 472 (M+1).

Example 162

N-[2,6-dimethylphenyl]3-(Isoxazolo[3,4-c]-1,2-Dihydro-3-methyl-6-chloroquinolin-2-on-1-yl)phenylacetamide Beginning with 3-(Isoxazolo[3,4-c]-1,2-dihydro-3-methyl-6-chloroquinolin-2-on-1-yl)phenylacetyl chloride and 2,6-dimethylaniline, the title compound was prepared essentially as described in Example 41.

MS(IS) m/z 472 (M+1).

Example 163

N-[3,4-dimethylphenyl]3-(Isoxazolo[3,4-c]-1,2-Dihydro-3-methyl-6-chloroquinolin-2-on-1-yl)phenylacetamide Beginning with 3-(Isoxazolo[3,4-c]-1,2-dihydro-3-methyl-6-chloroquinolin-2-on-1-yl)phenylacetyl chloride and 3,4-dimethylaniline, the title compound was prepared essentially as described in Example 41.

MS(IS) m/z 472 (M+1).

Example 164

N-[3,5-dimethylphenyl]3-(Isoxazolo[3,4-c]-1,2-Dihydro-3-methyl-6-chloroquinolin-2-on-1-yl)phenylacetamide Beginning with 3-(Isoxazolo[3,4-c]-1,2-dihydro-3-methyl-6-chloroquinolin-2-on-1-yl)phenylacetyl chloride and 3,5-methylaniline, the title compound was prepared essentially as described in Example 41.

MS(IS) m/z 472 (M+1).

Example 165

N-[2,4,6-trimethylphenyl]3-(Isoxazolo[3,4-c]-1,2-Dihydro-3-methyl-6-chloroquinolin-2-on-1-yl)phenylacetamide Beginning with 3-(Isoxazolo[3,4-c]-1,2-dihydro-3-methyl-6-chloroquinolin-2-on-1-yl)phenylacetyl chloride and 2,4,6-trimethylaniline, the title compound was prepared essentially as described in Example 41.

MS(IS) m/z 486 (M+1).

Example 166

N-[2,4,5-trimethylphenyl]3-(Isoxazolo[3,4-c]-1,2-Dihydro-3-methyl-6-chloroquinolin-2-on-1-yl)phenylacetamide Beginning with 3-(Isoxazolo[3,4-c]-1,2-dihydro-3-methyl-6-chloroquinolin-2-on-1-yl)phenylacetyl chloride and 2,4,5-trimethylaniline, the title compound was prepared essentially as described in Example 41.

MS(IS) m/z 486 (M+1).

Example 167

N-[2-methoxyphenyl]3-(Isoxazolo[3,4-c]-1,2-Dihydro-3-methyl-6-chloroquinolin-2-on-1-yl)phenylacetamide Beginning with 3-(Isoxazolo[3,4-c]-1,2-dihydro-3-methyl-6-chloroquinolin-2-on-1-yl)phenylacetyl chloride and 2-methoxyaniline, the title compound was prepared essentially as described in Example 41.

MS(IS) m/z 474 (M+1).

Example 168

N-[3-methoxyphenyl]3-(Isoxazolo[3,4-c]-1,2-Dihydro-3-methyl-6-chloroquinolin-2-on-1-yl)phenylacetamide Beginning with 3-(Isoxazolo[3,4-c]-1,2-dihydro-3-methyl-6-chloroquinolin-2-on-1-yl)phenylacetyl chloride and 3-methoxyaniline, the title compound was prepared essentially as described in Example 41.

MS(IS) m/z 474 (M+1).

Example 169

N-[2,3-dimethyoxyphenyl]3-(Isoxazolo[3,4-c]-1,2-Dihydro-3-methyl-6-chloroquinolin-2-on-1-yl)phenylacetamide Beginning with 3-(Isoxazolo[3,4-c]-1,2-dihydro-3-methyl-6-chloroquinolin-2-on-1-yl)phenylacetyl chloride and 2,3-dimethoxyaniline, the title compound was prepared essentially as described in Example 41.

MS(IS) m/z 504 (M+1).

Example 170

N-[2,4-dimethoxyphenyl]3-(Isoxazolo[3,4-c]-1,2-Dihydro-3-methyl-6-chloroquinolin-2-on-1-yl)phenylacetamide Beginning with 3-(Isoxazolo[3,4-c]-1,2-dihydro-3-methyl-6-chloroquinolin-2-on-1-yl)phenylacetyl chloride and 2,4-dimethoxyaniline, the title compound was prepared essentially as described in Example 41.

MS(IS) m/z 504 (M+1).

Example 171

N-[2,5-dimethoxyphenyl]3-(Isoxazolo[3,4-c]-1,2-Dihydro-3-methyl-6-chloroquinolin-2-on-1-yl)phenylacetamide Beginning with 3-(Isoxazolo[3,4-c]-1,2-dihydro-3-methyl-6-chloroquinolin-2-on-1-yl)phenylacetyl chloride and 2,5-dimethoxyaniline, the title compound was prepared essentially as described in Example 41.

MS(IS) m/z 504 (M+1).

Example 172

N-[3,4-(methylenedioxy)phenyl]3-(Isoxazolo[3,4-c]-1,2-Dihydro-3-methyl-6-chloroquinolin-2-on-1-yl)phenylacetamide Beginning with 3-(Isoxazolo[3,4-c]-1,2-dihydro-3-methyl-6-chloroquinolin-2-on-1-yl)phenylacetyl chloride and 3,4-(methylenedioxy)aniline, the title compound was prepared essentially as described in Example 41.

MS(IS) m/z 488 (M+1).

Example 173

N-[4-hydroxy-3,5-dimethoxyphenyl]3-(Isoxazolo[3,4-c]-1,2-Dihydro-3-methyl-6-chloroquinolin-2-on-1-yl)phenylacetimide Beginning with 3-(Isoxazolo[3,4-c]-1,2-dihydro-3-methyl-6-chloroquinolin-2-on-1-yl)phenylacetyl chloride and 4-hydroxy-3,5-dimethoxyaniline, the title compound was prepared essentially as described in. Example 41.

MS(IS) m/z 520 (M+1).

Example 174

N-[2-methoxy-6-methylphenyl]3-(Isoxazolo[3,4-c]-1,2-Dihydro-3-methyl-6-chloroquinolin-2-on-1-yl)phenylacetamide Beginning with 3-(Isoxazolo[3,4-c]-1,2-dihydro-3-methyl-6-chloroquinolin-2-on-1-yl)phenylacetyl chloride and 2-methoxy-6-methylaniline, the title compound was prepared essentially as described in Example 41.

MS(IS) m/z 488 (M+1).

Example 175

N-[3-methoxy-6-methylphenyl]3-(Isoxazolo[3,4-c]-1,2-Dihydro-3-methyl-6-chloroquinolin-2-on-1-yl)phenylacetamide Beginning with 3-(Isoxazolo[3,4-c]-1,2-dihydro-3-methyl-6-chloroquinolin-2-on-1-yl)phenylacetyl chloride and 3-methoxy-6-methylaniline, the title compound was prepared essentially as described in Example 41.

MS(IS) m/z 488 (M+1).

Example 176

N-[2-methyl-4-methoxyphenyl]3-(Isoxazolo[3,4-c]-1,2-Dihydro-3-methyl-6-chloroquinolin-2-on-1-yl)phenylacetamide Beginning with 3-(Isoxazolo[3,4-c]-1,2-dihydro-3-methyl-6-chloroquinolin-2-on-1-yl)phenylacetyl chloride and 2-methyl-4-methoxyaniline, the title compound was prepared essentially as described in Example 41.

MS(IS) m/z 488 (M+1).

Example 177

N-[2-methoxy-4-nitrophenyl]3-(Isoxazolo[3,4-c]-1,2-Dihydro-3-methyl-6-chloroquinolin-2-on-1-yl)phenylacetamide Beginning with 3-(Isoxazolo[3,4-c]-1,2-dihydro-3-methyl-6-chloroquinolin-2-on-1-yl)phenylacetyl chloride and 2-methoxy-4-nitroaniline, the title compound was prepared essentially as described in Example 41.

MS(IS) m/z 518 (M+1).

Example 178

N-[2-methoxy-5-nitrophenyl]3-(Isoxazolo[3,4-c]-1,2-Dihydro-3-methyl-6-chloroquinolin-2-on-1-yl)phenylacetamide Beginning with 3-(Isoxazolo[3,4-c]-1,2-dihydro-3-methyl-6-chloroquinolin-2-on-1-yl)phenylacetyl chloride and 2-methoxy-5-nitroaniline, the title compound was prepared essentially as described in Example 41.

MS(IS) m/z 518 (M+1).

Example 179

N-[2-nitrophenyl]3-(Isoxazolo[3,4-c]-1,2-Dihydro-3-methyl-6-chloroquinolin-2-on-1-yl)phenylacetamide Beginning with 3-(Isoxazolo[3,4-c]-1,2-dihydro-3-methyl-6-chloroquinolin-2-on-1-yl)phenylacetyl chloride and 2-nitroaniline, the title compound was prepared essentially as described in Example 41.

MS(IS) m/z 489 (M+1).

Example 180

N-[3-nitrophenyl]3-(Isoxazolo[3,4-c]-1,2-Dihydro-3-methyl-6-chloroquinolin-2-on-1-yl)phenylacetamide Beginning with 3-(Isoxazolo[3,4-c]-1,2-dihydro-3-methyl-6-chloroquinolin-2-on-1-yl)phenylacetyl chloride and 3-nitroaniline, the title compound was prepared essentially as described in Example 41.

MS(IS) m/z 489 (M+1).

Example 181

N-[3,5-dinitrophenyl]3-(Isoxazolo[3,4-c]-1,2-Dihydro-3-methyl-6-chloroquinolin-2-on-1-yl)phenylacetamide Beginning with 3-(Isoxazolo[3,4-c]-1,2-dihydro-3-methyl-6-chloroquinolin-2-on-1-yl)phenylacetyl chloride and 3,5-dinitroaniline, the title compound was prepared essentially as described in Example 41.

MS(IS) m/z 533 (M+1).

Example 182

N-[2-nitro-4-methoxyphenyl]3-(Isoxazolo[3,4-c]-1,2-Dihydro-3-methyl-6-chloroquinolin-2-on-1-yl)phenylacetamide Beginning with 3-(Isoxazolo[3,4-c]-1,2-dihydro-3-methyl-6-chloroquinolin-2-on-1-yl)phenylacetyl chloride and 2-nitro-4-methoxyaniline, the title compound was prepared essentially as described in Example 41.

MS(IS) m/z 519 (M+1).

Example 183

N-[2-fluorophenyl]3-(Isoxazolo[3,4-c]-1,2-Dihydro-3-methyl-6-chloroquinolin-2-on-1-yl)phenylacetamide Beginning with 3-(Isoxazolo[3,4-c]-1,2-dihydro-3-methyl-6-chloroquinolin-2-on-1-yl)phenylacetyl chloride and 2-fluoroaniline, the title compound was prepared essentially as described in Example 41.

MS(IS) m/z 462 (M+1).

Example 184

N-[3-fluorophenyl]3-(Isoxazolo[3,4-c]-1,2-Dihydro-3-methyl-6-chloroquinolin-2-on-1-yl)phenylacetamide Beginning with 3-(Isoxazolo[3,4-c]-1,2-dihydro-3-methyl-6-chloroquinolin-2-on-1-yl)phenylacetyl chloride and 3-fluoroaniline, the title compound was prepared essentially as described in Example 41.

MS(IS) m/z 462 (M+1).

Example 185

N-[2,3-difluorophenyl]3-(Isoxazolo[3,4-c]-1,2-Dihydro-3-methyl-6-chloroquinolin-2-on-1-yl)phenylacetamide Beginning with 3-(Isoxazolo[3,4-c]-1,2-dihydro-3-methyl-6-chloroquinolin-2-on-1-yl)phenylacetyl chloride and 2,3-difluoroaniline, the title compound was prepared essentially as described in Example 41.

MS(IS) m/z 480 (M+1).

Example 186

N-[2,4-difluorophenyl]3-(Isoxazolo[3,4-c]-1,2-Dihydro-3-methyl-6-chloroquinolin-2-on-1-yl)phenylacetamide Beginning with 3-(Isoxazolo[3,4-c]-1,2-dihydro-3-methyl-6-chloroquinolin-2-on-1-yl)phenylacetyl chloride and 2,4-difluoroaniline, the title compound was prepared essentially as described in Example 41.

MS(IS) m/z 480 (M+1).

Example 187

N-[2,5-difluorophenyl]3-(Isoxazolo[3,4-c]-1,2-Dihydro-3-methyl-6-chloroquinolin-2-on-1-yl)phenylacetamide Beginning with 3-(Isoxazolo[3,4-c]-1,2-dihydro-3-methyl-6-chloroquinolin-2-on-1-yl)phenylacetyl chloride and 2,5-difluoroaniline, the title compound was prepared essentially as described in Example 41.

MS(IS) m/z 480 (M+1).

Example 188

N-[2,6-difluorophenyl]3-(Isoxazolo[3,4-c]-1,2-Dihydro-3-methyl-6-chloroquinolin-2-on-1-yl)phenylacetamide Beginning with 3-(Isoxazolo[3,4-c]-1,2-dihydro-3-methyl-6-chloroquinolin-2-on-1-yl)phenylacetyl chloride and 2,6-difluoroaniline, the title compound was prepared essentially as described in Example 41.

MS(IS) m/z 480 (M+1).

Example 189

N-[3,4-difluorophenyl]3-(Isoxazolo[3,4-c]-1,2-Dihydro-3-methyl-6-chloroquinolin-2-on-1-yl)phenylacetamide Beginning with 3-(Isoxazolo[3,4-c]-1,2-dihydro-3-methyl-6-chloroquinolin-2-on-1-yl)phenylacetyl chloride and 3,4-difluoroaniline, the title compound was prepared essentially as described in Example 41.

MS(IS) m/z 480 (M+1).

Example 190

N-[3,5-difluorophenyl]3-(Isoxazolo[3,4-c]-1,2-Dihydro-3-methyl-6-chloroquinolin-2-on-1-yl)phenylacetamide Beginning with 3-(Isoxazolo[3,4-c]-1,2-dihydro-3-methyl-6-chloroquinolin-2-on-1-yl)phenylacetyl chloride and 3,5-difluoroaniline, the title compound was prepared essentially as described in Example 41.

MS(IS) m/z 480 (M+1).

Example 191

N-[2,3,4-trifluorophenyl]3-(Isoxazolo[3,4-c]-1,2-Dihydro-3-methyl-6-chloroquinolin-2-on-1-yl)phenylacetamide Beginning with 3-(Isoxazolo[3,4-c]-1,2-dihydro-3-methyl-6-chloroquinolin-2-on-1-yl)phenylacetyl chloride and 2,3,4-trifluoroaniline, the title compound was prepared essentially as described in Example 41.

MS(IS) m/z 498 (M+1).

Example 192

N-[2,3,6-trifluorophenyl]3-(Isoxazolo[3,4-c]-1,2-Dihydro-3-methyl-6-chloroquinolin-2-on-1-yl)phenylacetamide Beginning with 3-(Isoxazolo[3,4-c]-1,2-dihydro-3-methyl-6-chloroquinolin-2-on-1-yl)phenylacetyl chloride and 2,3,6-trifluoroaniline, the title compound was prepared essentially as described in Example 41.

MS(IS) m/z 498 (M+1).

Example 193

N-[2,4,5-trifluorophenyl]3-(Isoxazolo[3,4-c]-1,2-Dihydro-3-methyl-6-chloroquinolin-2-on-1-yl)phenylacetamide Beginning with 3-(Isoxazolo[3,4-c]-1,2-dihydro-3-methyl-6-chloroquinolin-2-on-1-yl)phenylacetyl chloride and 2,4,5-trifluoroaniline, the title compound was prepared essentially as described in Example 41.

MS(IS) m/z 498 (M+1).

Example 194

N-[2,4,6-trifluorophenyl]3-(Isoxazolo[3,4-c]-1,2-Dihydro-3-methyl-6-chloroquinolin-2-on-1-yl)phenylacetamide Beginning with 3-(Isoxazolo[3,4-c]-1,2-dihydro-3-methyl-6-chloroquinolin-2-on-1-yl)phenylacetyl chloride and 2,4,6-trifluoroaniline, the title compound was prepared essentially as described in Example 41.

MS(IS) m/z 498 (M+1).

Example 195

N-[2,3,4,5-tetrafluorophenyl]3-(Isoxazolo[3,4-c]-1,2-Dihydro-3-methyl-6- chloroquinolin-2-on-1-yl)phenylacetamide Beginning with 3-(Isoxazolo[3,4-c]-1,2-dihydro-3-methyl-6-chloroquinolin-2-on-1-yl)phenylacetyl chloride and 2,3,4,5-tetrafluoroaniline, the title compound was prepared essentially as described in Example 41.

MS(IS) m/z 516 (M+1).

Example 196

N-[2,3,4,6-tetrafluorophenyl]3-(Isoxazolo[3,4-c]-1,2-Dihydro-3-methyl-6-chloroquinolin-2-on-1-yl)phenylacetamide Beginning with 3-(Isoxazolo[3,4-c]-1,2-dihydro-3-methyl-6-chloroquinolin-2-on-1-yl)phenylacetyl chloride and 2,3,4,6-tetrafluoroaniline, the title compound was prepared essentially as described in Example 41.

MS(IS) m/z 516 (M+1).

Example 197

N-[2,3,5,6-tetrafluorophenyl]3-(Isoxazolo[3,4-c]-1,2-Dihydro-3-methyl-6-chloroquinolin-2-on-1-yl)phenylacetamide Beginning with 3-(Isoxazolo[3,4-c]-1,2-dihydro-3-methyl-6-chloroquinolin-2-on-1-yl)phenylacetyl chloride and 2,3,5,6-tetrafluoroaniline, the title compound was prepared essentially as described in Example 41.

MS(IS) m/z 516 (M+1).

Example 198

N-[3-fluoro-4-methoxyphenyl]3-(Isoxazolo[3,4-c]-1,2-Dihydro-3-methyl-6-chloroquinolin-2-on-1-yl)phenylacetamide Beginning with 3-(Isoxazolo[3,4-c]-1,2-dihydro-3-methyl-6-chloroquinolin-2-on-1-yl)phenylacetyl chloride and 3-fluoro-4-methoxyaniline, the title compound was prepared essentially as described in Example 41.

MS(IS) m/z 492 (M+1).

Example 199

N-[4-tert-butylphenyl]3-(Isoxazolo[3,4-c]-1,2-Dihydro-3-methyl-6-chloroquinolin-2-on-1-yl)phenylacetamide Beginning with 3-(Isoxazolo[3,4-c]-1,2-dihydro-3-methyl-6-chloroquinolin-2-on-1-yl)phenylacetyl chloride and 4-tert-butylaniline, the title compound was prepared essentially as described in Example 41.

MS(IS) m/z 500 (M+1).

Example 200

N-[4-cyclohexylphenyl]3-(Isoxazolo[3,4, -c]-1,2-Dihydro-3-methyl-6-chloroquinolin-2-on-1-yl)phenylacetamide Beginning with 3-(Isoxazolo[3,4-c]-1,2-dihydro-3-methyl-6-chloroquinolin-2-on-1-yl)phenylacetyl chloride and 4-cyclohexylaniline, the title compound was prepared essentially as described in Example 41.

MS(IS) m/z 526 (M+1).

Example 201

N-[4-acetylphenyl]3-(Isoxazolo[3,4-c]-1,2-Dihydro-3-methyl-6-chloroquinolin-2-on-1-yl)phenylacetamide Beginning with 3-(Isoxazolo[3,4-c]-1,2-dihydro-3-methyl-6-chloroquinolin-2-on-1-yl)phenylacetyl chloride and 4-acetylaniline, the title compound was prepared essentially as described in Example 41.

MS(IS) m/z 486 (M+1).

Example 202

N-[4-cyanophenyl]3-(Isoxazolo[3,4-c]-1,2-Dihydro-3-methyl-6-chloroquinolin-2-on-1-yl) phenylacetamide Beginning with 3-(Isoxazolo[3,4-c]-1,2-dihydro-3-methyl-6-chloroquinolin-2-on-1-yl)phenylacetyl chloride and 4-cyanoaniline, the title compound was prepared essentially as described in Example 41.

MS(IS) m/z 469 (M+1).

Example 203

N-[4-carboxamidophenyl]3-(Isoxazolo[3,4-c]-1,2-Dihydro-3-methyl-6-chloroquinolin-2-on-1-yl) phenylacetamide Beginning with 3-(Isoxazolo[3,4-c]-1,2-dihydro-3-methyl-6-chloroquinolin-2-on-1-yl)phenylacetyl chloride and 4-carboxamidoaniline, the title compound was prepared essentially as described in Example 41.

MS(IS) m/z 587 (M+1).

Example 204

N-[4-(N',N'-dipropylsulfonamido)phenyl]3-(Isoxazolo[3,4-c]-1,2-Dihydro-3-methyl-6-chloroquinolin-2-on-1-yl) phenylacetamide Beginning with 3-(Isoxazolo[3,4-c]-1,2-dihydro-3-methyl-6-chloroquinolin-2-on-1-yl)phenylacetyl chloride and 4-(N',N'-dipropylsulfonamido)aniline, the title compound was prepared essentially as described in Example 41.

MS(IS) m/z 606 (M−1).

Example 205

N-[3,5-di(trifluoromethyl)phenyl]3-(Isoxazolo[3,4-c]-1,2-Dihydro-3-methyl-6-chloroquinolin-2-on-1-yl)phenylacetamide Beginning with 3-(Isoxazolo[3,4-c]-1,2-dihydro-3-methyl-6-chloroquinolin-2-on-1-yl)phenylacetyl chloride and 3,5-di(trifluoromethyl)aniline, the title compound was prepared essentially as described in Example 41.

MS(IS) m/z 580 (M+1).

Example 206

N-[3-trifluoromethyl-5-methoxyphenyl]3-(Isoxazolo[3,4-c]-1,2-Dihydro-3-methyl-6-chloroquinolin-2-on-1-yl)phenylacetamide Beginning with 3-(Isoxazolo[3,4-c]-1,2-dihydro-3-methyl-6-chloroquinolin-2-on-1-yl)phenylacetyl chloride and 3-trifluoromethyl-5-methoxyaniline, the title compound was prepared essentially as described in Example 41.

MS(IS) m/z 542 (M+1).

Example 207

N-[2-methoxy-5-tert-butylphenyl]3-(Isoxazolo[3,4-c]-1,2-Dihydro-3-methyl-6-chloroquinolin-2-on-1-yl)phenylacetamide Beginning with 3-(Isoxazolo[3,4-c]-1,2-dihydro-3-methyl-6-chloroquinolin-2-on-1-yl)phenylacetyl chloride and 2-methoxy-5-tert-butylaniline, the title compound was prepared essentially as described in Example 41.

MS(IS) m/z 530 (M+1).

Example 208

N-[3,5-dimethoxybenzyl]3-(Isoxazolo[3,4-c]-1,2-Dihydro-3-methyl-6-chloroquinolin-2-on-1-yl) phenylacetamide Beginning with 3-(Isoxazolo[3,4-c]-1,2-dihydro-3-methyl-6-chloroquinolin-2-on-1-yl)phenylacetyl chloride and 3,5-dimethoxybenzylamine, the title compound was prepared essentially as described in Example 41.

MS(IS) m/z 518 (M+1).

Example 209

N-[naphth-2-yl]3-(Isoxazolo[3,4-c]-1,2-Dihydro-3-methyl-6-chloroquinolin-2-on-1-yl)phenylacetamide Beginning with 3-(Isoxazolo[3,4-c]-1,2-dihydro-3-methyl-6-chloroquinolin-2-on-1-yl)phenylacetyl chloride and 2-aminonapthalene, the title compound was prepared essentially as described in Example 41.

MS (IS) m/z 494 (M+1).

Example 210

N-methyl N-[3,4,5-trimethoxyphenyl]3-(Isoxazolo[3,4-c]-1,2-Dihydro-3-methyl-6-chloroquinolin-2-on-1-yl)phenylacetamide Beginning with 3-(Isoxazolo[3,4-c]-1,2-dihydro-3-methyl-6-chloroquinolin-2-on-1-yl)phenylacetyl chloride and N-methyl 3,4,5-trimethoxyaniline, the title compound was prepared essentially as described in Example 41.

MS(IS) m/z 548 (M+1).

Example 211

N-[3,4,5-trimethoxyphenyl]2-(Isoxazolo[3,4-c]-1,2-Dihydro-3-methyl-6-chloroquinolin-2-on-1-yl) phenylacetamide Beginning with 2-(Isoxazolo[3,4-c]-1,2-dihydro-3-methyl-6-chloroquinolin-2-on-1-yl)phenylacetyl chloride and 3,4,5-trimethoxyaniline, the title compound was prepared essentially as described in Example 33.

MS(IS) m/z 534 (M+1).

Example 212

N-[3,4,5-trimethoxyphenyl]2-(Isoxazolo[3,4-c]-1,2-Dihydro-3-methyl-6-chloroquinolin-2-on-1-yl) phenylpropionamide Beginning with 2-(Isoxazolo[3,4-c]-1,2-dihydro-3-methyl-6-chloroquinolin-2-on-1-yl)phenylpropionyl chloride and 3,4,5-trimethoxyaniline, the title compound was prepared essentially as described in Example 33.

MS(IS) m/z 548 (M+1).

Example 213

N-[3,4,5-trimethoxyphenyl]4-(Isoxazolo[3,4-c]-1,2-Dihydro-3-methyl-6-chloroquinolin-2-on-1-yl) benzamide Beginning with 4-(Isoxazolo[3,4-c]-1,2-dihydro-3-methyl-6-chloroquinolin-2-on-1-yl)benzoyl chloride and

Example 214

N-[3,4,5-trimethoxyphenyl]4-(Isoxazolo[3,4-c]-1,2-Dihydro-3-methyl-6-chloroquinolin-2-on-1-yl)phenylacetamide Beginning with 4-(Isoxazolo[3,4-c]-1,2-dihydro-3-methyl-6-chloroquinolin-2-on-1-yl)phenylacetyl chloride and 3,4,5-trimethoxyaniline, the title compound was prepared essentially as described in Example 33.

MS(IS) m/z 534 (M+1).

Example 215

N-[3,4,5-trimethoxyphenyl]2-hydroxy-5-(Isoxazolo[3,4-c]-1,2-Dihydro-3-methyl-6-chloroquinolin-2-on-1-yl phenylacetamide Beginning with 2-hydroxy-5-(Isoxazolo[3,4-c]-1,2-dihydro-3-methyl-6-chloroquinolin-2-on-1-yl)phenylacetyl chloride and 3,4,5-trimethoxyaniline, the title compound was prepared essentially as described in Example 33.

MS(IS) m/z 550 (M+1).

Example 216

N-[3,4,5-trimethoxyphenyl]2-methoxy-5-(Isoxazolo[3,4-c]-1,2-Dihydro-3-methyl-6-chloroquinolin-2-on-1-yl)phenylacetamide Beginning with 2-methoxy-5-(Isoxazolo[3,4-c]-1,2-dihydro-3-methyl-6-chloroquinolin-2-on-1-yl)phenylacetyl chloride and 3,4,5-trimethoxyaniline, the title compound was prepared essentially as described in Example 33.

MS(IS) m/z 564 (M+1).

Example 217

N-[3,4,5-trimethoxyphenyl]2-benzyloxy-5-(Isoxazolo[3,4-c]-1,2-Dihydro-3-methyl-6-chloroquinolin-2-on-1-yl)phenylacetamide Beginning with 2-benzyloxy-5-(Isoxazolo[3,4-c]-1,2-dihydro-3-methyl-6-chloroquinclin-2-on-1-yl)phenylacetyl chloride and 3,4,5-trimethoxyaniline, the title compound was prepared essentially as described in Example 33.

MS(IS) m/z 640 (M+1).

Example 218

N-[3,4,5-trimethoxyphenyl]2-cyclohexylmethoxy-5-(Isoxazolo[3,4-c]-1,2-Dihydro-3-methyl-6-chloroquinolin-2-on-1-yl)phenylacetamide Beginning with 2-cyclohexylmethoxy-5-(Isoxazolo[3,4-c]-1,2-dihydro-3-methyl-6-chloroquinolin-2-on-1-yl) phenylacetyl chloride and 3,4,5-trimethoxyaniline, the title compound was prepared essentially as described in Example 33.

MS(IS) m/z 644 (M+1).

Example 219

N-methyl N-[3,4,5-trimethoxybenzoyl]3-(Isoxazolo[3,4-c]-1,2-Dihydro-3-methyl-6-chloroquinolin-2-on-1-yl)benzylamine Beginning with N-methyl 3-(Isoxazolo[3,4-c]-1,2-Dihydro-3-methyl-6-chloroquinolin-2-on-1-yl)benzylamine and 3,4,5-trimethoxybenzoyl chloride, the title compound was prepared essentially as described in the General Procedures for Examples 83–119.

MS(IS) m/z 548 (M+1).

Example 220

N-[4-methyl-3,5-dimethoxybenzoyl]3-(Isoxazolo[3,4-c]-1,2-Dihydro-3-methyl-6-chloroquinolin-2-on-1-yl)benzylamine Beginning with 3-(Isoxazolo[3,4-c]-1,2-Dihydro-3-methyl-6-chloroquinolin-2-on-1-yl)benzylamine and 4-methyl-3,5-dimethoxybenzoyl chloride, the title compound was prepared essentially as described in the General Procedures for Examples 83–119.

MS(IS) m/z 518 (M+1).

Example 221

N-[3,4,5-trimethoxybenzoyl]3-(Isoxazolo[3,4-c]-1,2-Dihydro-3-methyl-6-chloroquinolin-2-on-1-yl)aniline Beginning with 3-(Isoxazolo[3,4-c]-1,2-Dihydro-3-methyl-6-chloroquinolin-2-on-1-yl)aniline and 3,4,5-trimethoxybenzoyl chloride, the title compound was prepared essentially as described in the General Procedures for Examples 83–119.

MS(IS) m/z 520 (M+1).

Example 222

N-[3,4,5-trimethoxyphenylglyoxyloyl]3-(Isoxazolo[3,4-c]-1,2-Dihydro-3-methyl-6-chloroquinolin-2-on-1-yl)aniline Beginning with 3-(Isoxazolo[3,4-c]-1,2-Dihydro-3-methyl-6-chloroquinolin-2-on-1-yl)aniline and 3,4,5-trimethoxyglyoxyloyl chloride, the title compound was prepared essentially as described in the General Procedures for Examples 83–119.

MS(IS) m/z 548 (M+1).

Example 223

1-(3-(Isoxazolo[3,4-c]-1,2-Dihydro-3-methyl-6-chloroquinolin-2-on-1-yl)-2-(2-(N-[3,4,5-trimethoxybenzoyl]aminocarbonyl)phenyl)ethane Beginning with 1-(3-(Isoxazolo[3,4-c]-1,2-Dihydro-3-methyl-6-chloroquinolin-2-on-1-yl)-2-(2-(chlorocarbonyl)-phenyl)ethane and 3,4,5-trimethoxyaniline, the title compound was prepared essentially as described in Example 33.

MS(IS) m/z 520 (M+1).

The compounds of the invention are inhibitors of MRP1. Thus, the compounds of the invention may be used to inhibit any neoplasm having intrinsic and/or acquired resistance, conferred in part or in total by MRP1, to an oncolytic or oncolytics. In other words, treatment of such a neoplasm with an effective amount of a compound of this invention will cause the neoplasm to be more sensitive to chemotherapy that was rendered less efficacious by MRP1.

Vincristine, epirubicin, daunorubicin, doxorubicin, and etoposide are oncolytics that are substrates of MRP1. See Cole, et. al., "Pharmacological Characterization of Multidrug Resistant MRP-transfected Human Tumor Cells", *Cancer Research*, 54:5902–5910, 1994. Since MRP1 is ubiquitous in mammals, particularly humans, Nooter, K, et. al., "Expression of the Multidrug Resistance-Associated Protein (MRP) Gene in Human Cancers", *Clin. Can. Res.*, 1:1301–1310, (1995), chemotherapy whose goal is to inhibit a neoplasm employing any of those agents has the potential to be rendered less efficacious by MRP1. Thus, neoplasms of the bladder, bone, breast, lung(small-cell), testis, and thyroid and more specific types of cancer such as acute lymphoblastic and myeloblastic leukemia, Wilm's tumor, neuroblastoma, soft tissue sarcoma, Hodgkin's and non-Hodgkin's lymphomas, and bronchogenic carcinoma may be inhibited with a combination of one or more of the above oncolytics and a compound of this invention.

The biological activity of the compounds of the present invention was evaluated employing an initial screening assay which rapidly and accurately measured the activity of the tested compound in inhibiting MRP1 or MDR1. Assays useful for evaluating this reversing capability are well known in the art. See, e.g., T. McGrath, et al., *Biochemical Pharmacology*, 38:3611, 1989; D. Marquardt and M. S. Center, *Cancer Research*, 52:3157, 1992; D. Marquardt, et al., *Cancer Research*, 50:1426, 1990; and Cole, et. al., *Cancer Research*, 54: 5902–5910, 1994.

Assay for Reversal of MRP1-Mediated Doxorubicin Resistance and MDR1-Mediated Vincristine Resistance: HL60/ADR and HL60/VCR are continuous cell lines, which were selected for doxorubicin and vincristine resistance respectively by culturing HL60, a human acute myeloblastic leukemia cell line, in increasing concentrations of doxorubicin or vincristine until a highly resistant variant was attained.

HL60/ADR and HL60/VCR cells were grown in RPMI 1640 (Gibco) containing 10 fetal bovine serum (FBS) and 250 $\mu$g/ml GENTAMICIN™ (Sigma). Cells were harvested; washed twice with assay medium (same as culture media); counted; and diluted to $2\times10^5$ cells/ml in assay medium. Fifty microliters of cells were aliquoted into wells of a 96 well tissue culture plate. One column of each 96 well plate served as a negative control and received assay medium containing no cells.

Test compounds and reference compounds were dissolved in dimethyl sulfoxide (DMSO) at a concentration of 5 mM. Samples were diluted to 20 $\mu$M in assay medium and 25 $\mu$l of each test compound was added to 6 wells. Assay standards were run in quadruplicate. Twenty-five microliters of 0.4% DMSO was added to four wells as a solvent control. Assay media was added to all wells to achieve a final volume of 100 $\mu$l per well.

The plates were incubated at 37° C. for 72 hours in a humidified incubator with a 5% carbon dioxide atmosphere. Cell viability and vitality was measured by oxidation of a tetrazolium salt using standard conditions. The plates were incubated for 3 hours at 37° C. Absorbance was determined at 490 nm using a microtitre plate reader.

The ability of a test compound to reverse the resistance of HL60/ADR and HL60/VCR cells to doxorubicin was determined by comparison of the absorbance of the wells containing a test compound in addition to the oncolytic (doxorubicin) with the absorbance of wells containing the oncolytic without a test compound. Controls were used to eliminate background and to ensure the results were not artifactual. The results of the assay are expressed as percent inhibition of cell growth. The oncolytic alone at the tested concentration does not usually inhibit the growth of EL60/ADR or HL60/VCR cells.

Representative compounds of formula I demonstrated a significant effect in reversing the MRP1 multiple drug resistance. Many of the compounds showed very significant enhancement of activity in combination with the oncolytic agent as opposed to the oncolytic agent alone. In addition, a large majority of the compounds tested displayed a significant degree of selective inhibition of the HL60/ADR cell line over the HL60/VCR cell line.

When administering an oncolytic in practicing the methods of this invention, the amount of oncolytic employed will be variable. It should be understood that the amount of the oncolytic actually administered will be determined by a physician, in the light of the relevant circumstances, including the condition to be treated, the chosen route of administration, the actual oncolytic administered, the age, weight, and response of the individual patient (mammal), and the severity of the patient's symptoms. Of course, the amount of oncolytic administered should be decided and closely monitored by that patient's physician. After deciding on the oncolytic or oncolytics to employ, "The Physician's Desk Reference®", published by Medical Economics Company at Montvale, N.J. 07645–1742, is a helpful resource to the physician in deciding on amounts of the oncolytic to administer and is updated annually.

Preferred formulations, and the methods of this invention employing those formulations, are those which do not contain an oncolytic. Thus, it is preferred to administer the compounds of this invention separately from the oncolytic. The oncolytics mentioned in this specification are commercially available and may be purchased in pre-formulated forms suitable for the methods of this invention.

The compounds of formula I alone, or optionally in acombination with an oncolytic, are usually administered in the form of pharmaceutical formulations. These formulations can be administered by a variety of routes including oral, rectal, transdermal, subcutaneous, intravenous, intramuscular, and intranasal. Such formulations are prepared in a manner well known in the pharmaceutical art and comprise at least one active compound of formula I.

The present invention also includes methods employing pharmaceutical formulations which contain, as the active ingredient, the compounds of formula I, and optionally an oncolytic, associated with pharmaceutical carriers. In making the formulations of the present invention the active ingredient(s) is usually mixed with an excipient, diluted by an excipient, or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the formulations can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound(s) to provide the appropriate particle size prior to combining with the other ingredients. If the active compound(s) is substantially insoluble, it ordinarily is milled to a particle size of less than 200 mesh. If the active compound(s) is substantially water soluble, the particle size is normally adjusted by milling to provide a substantially uniform distribution in the formulation, e.g., about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The formulations of the invention can be formulated so as to provide quick, sustained or delayed release of the active ingredient after administration to the patient by employing procedures known in the art.

The formulations are preferably formulated in a unit dosage form, each dosage containing from about 5 to about 100 mg, more usually about 10 to about 30 mg, of each active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The compounds of formula I are effective over a wide dosage range. For example, dosages per day normally fall within the range of about 0.5 to about 30 mg/kg of body weight. In the treatment of adult humans, the range of about 1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

For preparing solid formulations such as tablets the principal active ingredient(s) is mixed with a pharmaceutical excipient to form a solid preformulation composition containing a homogeneous mixture of a compound of the present invention. When referring to these preformulation compositions as homogeneous, it is meant that the active ingredient(s) is dispersed evenly throughout the formulation so that the formulation may be readily subdivided into equally effective unit dosage forms such as tablets, pills and capsules. This solid preformulation is then subdivided into unit dosage forms of the type described above containing from 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by enteric layer which serves to resist disintegration in the stomach and permit the inner component to pass intact into the aduodenum or to be delayed in release. A variety of materials can be used for such enteric layers or coatings, such materials including a number of polymeric acids and mixtures of polymeric acids with such materials as shellac, cetyl alcohol, and cellulose acetate.

The novel formulations which are liquid forms may be incorporated for administration orally or by injection and include aqueous solutions, suitably flavored syrups, aqueous or oil suspensions, and flavored emulsions with edible oils such as cottonseed oil, sesame oil, coconut oil, or peanut Th oil, as well as elixirs and similar pharmaceutical vehicles.

Formulations for inhalation or insufflation include solutions and suspensions in pharmaceutical, aqueous or organic solvents, or mixtures thereof, and powders. The liquid or solid formulations may contain suitable pharmaceutical excipients as described supra. Preferably the formulations are administered by the oral or nasal respiratory route for local or systemic effect. Compositions in preferably pharmaceutical solvents may be nebulized by use of inert gases. Nebulized solutions may be breathed directly from the nebulizing device or the nebulizing device may be attached to a face mask, tent, or intermittent positive pressure breathing machine. Solution, suspension, or powder formulations may be administered, preferably orally or nasally, from devices which deliver the formulation in an appropriate manner.

The following formulation examples are illustrative only and are not intended to limit the scope of the invention in any way. "Active ingredient(s)" means a compound according to formula I or a pharmaceutical salt or solvate thereof optionally with one or more oncolytics.

Formulation Example 1

Hard gelatin capsules containing the following ingredients are prepared:

| Ingredient | Quantity (mg/capsule) |
| --- | --- |
| Active Ingredient (s) | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/tablet) |
| --- | --- |
| Active Ingredient (s) | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

A dry powder inhaler formulation is prepared containing the following components:

| Ingredient | Weight % |
| --- | --- |
| Active Ingredient (s) | 5 |
| Lactose | 95 |

The active ingredient is mixed with the lactose and the mixture is added to a dry powder inhaling appliance.

Formulation Example 4

Tablets, each containing 30 mg of active ingredient, are prepared as follows:

| Ingredient | Quantity (mg/tablet) |
|---|---|
| Active Ingredient (s) | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Example 5

Capsules, each containing 40 mg of medicament are made as follows:

| Ingredient | Quantity (mg/capsule) |
|---|---|
| Active Ingredient (s) | 40.0 mg |
| Starch | 109.0 mg |
| Magnesium stearate | 1.0 mg |
| Total | 150.0 mg |

The active ingredient, cellulose, starch, and magnesium stearate are blended, passed through a No. 20 mesh U.S. sieve, and filled into hard gelatin capsules in 150 mg quantities.

Formulation Example 6

Suppositories, each containing 25 mg of active ingredient are made as follows:

| Ingredient | Amount |
|---|---|
| Active Ingredient (s) | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of medicament per 5.0 ml dose are made as follows:

| Incredient | Amount |
|---|---|
| Active Ingredient (s) | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

Capsules, each containing 15 mg of medicament, are made as follows:

| Ingredient | Quantity (mg/capsule) |
|---|---|
| Active Ingredient (s) | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 425 mg quantities.

Formulation Example 9

An intravenous formulation may be prepared as follows:

| Ingredient | Quantity |
|---|---|
| Active Ingredient (s) | 250.0 mg |
| Isotonic saline | 1000 ml |

Formulation Example 10

A topical formulation may be prepared as follows:

| Ingredient | Quantity |
|---|---|
| Active Ingredient (s) | 1–10 g |
| Emulsifying Wax | 30 g |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Formulation Example 11

Sublingual or buccal tablets, each containing 10 mg of active ingredient, may be prepared as follows:

| Ingredient | Quantity Per Tablet |
| --- | --- |
| Active Ingredient (s) | 10.0 mg |
| Glycerol | 210.5 mg |
| Water | 143.0 mg |
| Sodium Citrate | 4.5 mg |
| Polyvinyl Alcohol | 26.5 mg |
| Polyvinylpyrrolidone | 15.5 mg |
| Total | 410.0 mg |

The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50–55° C. and the active ingredient is slowly admixed. The homogenous mixture is poured into forms made of an inert material to produce a drug-containing diffusion matrix having a thickness of about 2–4 mm. This diffusion matrix is then cut to form individual tablets having the appropriate size.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical formulation to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intraarterial infusion of hypertonic solutions which can transiently open the bloodbrain barrier.

We claim:
1. A compound of formula I:

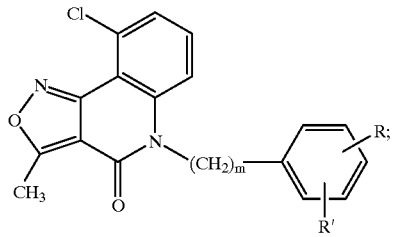

where:
R is $(CH_2)_m$, $CHR^1NHR^2$, $O(CH_2)_2NR^2$, $(CH_2)_mCOR^3$, $NHR^2$, and $(CH_2)_m$, $CHR^1NR^4R^5$;
R' is hydrogen, hydroxy, or $O(C_1-C_6$ alkyl optionally substituted with phenyl or $C_3-C_7$ cycloalkyl);
m and m' are independently at each occurrence 0, 1, or 2;
$R^1$ is independently at each occurrence hydrogen or $C_1-C_6$ alkyl;
$R^2$ is hydrogen, $COR^6$, $CH_2R^{6'}$, $SO_2R^7$, or a moiety of the formula

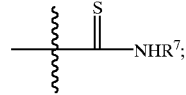

$R^3$ is hydrogen, hydroxy, $C_1-C_6$ alkoxy, an amino ester, an amino acid, or $NR^4R^5$;
$R^4$ is hydrogen or $C_1-C_6$ alkyl;
$R^5$ is hydrogen, $C_1-C_6$ alkyl, $C_6-C_{10}$ bicycloalkyl, $CH_2CH(CH_3)$phenyl, $CH(CH_3)CH_2CO_2R^1$, aryl, substituted aryl, or $R^4$ and $R^5$ combine to form a pyrrolidin-1-yl or piperidin-1-yl;
n is 1, 2, 3, or 4;
q is 0, 1, 2, or 3;
$R^6$ is $C_1-C_6$ alkyl, substituted $C_3-C_6$; cycloalkyl, aryl, substituted aryl, or tert-butoxy;
$R^{6'}$ is $C_1-C_6$ alkyl, substituted $C_3-C_6$ cycloalkyl, aryl, or substituted aryl;
r is 0, 1, or 2;
$R^7$ is $C_1-C_6$ alkyl, phenyl or substituted phenyl; and $R^8$ is hydrogen or $CO_2R^1$; or a pharmaceutical salt or solvate thereof.

2. The compound according to claim 1 where m is 0 and m' is 0 or 1 and R is at the meta position, or a pharmaceutical salt or solvate thereof.

3. The compound according to claim 2 where R is $CHR^1NHR^2$ and $R^1$ is methyl, or a pharmaceutical salt or solvate thereof.

4. The compound according to claim 3 where $R^2$ is 4-aminosulfonylbenzyl or 3,4,5-trimethoxybenzyl, or a pharmaceutical salt or solvate thereof.

5. The compound according to claim 2 where R is $COR^3$ or $(CH_2)COR^3$, or a pharmaceutical salt or solvate thereof.

6. The compound according to claim 5 where $R^3$ is (3,4,5-trimethoxyphenyl)amino, or (4-aminosulfonylphenyl)amino, or a pharmaceutical salt or solvate thereof.

7. The compound according to claim 2 where R is $(CH_2)NR^4R^5$ and $R^4$ is hydrogen, or a pharmaceutical salt or solvate thereof.

8. The compound according to claim 7 where $R^5$ is 3,4,5-trimethoxybenzoyl, 3,5-dimethoxy-4- hydroxybenzoyl, or 3,4,5-trimethoxybenzyl, or a pharmaceutical salt or solvate thereof.

9. A method of inhibiting MRP1 in a mammal which comprises administering to a mammal in need thereof an effective amount of a compound of formula I:

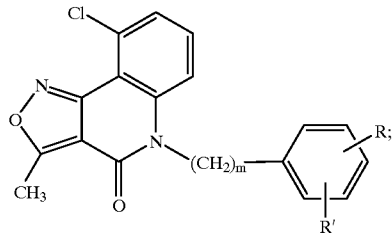

where:
R is $(CH_2)_m$, $CHR^1NHR^2$, $O(CH_2)_2NHR^2$ $(CH_2)_m$, $COR^3NHR^2$, and $(CH_2)_{m'}$, $CHR^1NH^4R^5$;
R' is hydrogen, hydroxy, or ($C_1$–$C_6$ alkyl optionally substituted with phenyl or $C_3$–$C_7$ cycloalkyl);
m and m' are independently at each occurrence 0, 1, or 2;
  $R^1$ is independently at each occurrence hydrogen or $C_1$–$C_6$ alkyl;
  $R^2$ is hydrogen, $COR^6$, $CH_2R^{6'}$, $SO_2R^7$, or a moiety of the formula

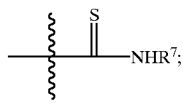

$R^3$ is hydrogen, hydroxy, $C_1$–$C_6$ alkoxy, an amino ester, an amino acid, or $NR^4R^5$;
$R^4$ is hydrogen or $C_1$–$C_6$ alkyl;
$R^5$ is hydrogen, $C_1$–$C_6$ alkyl, $C_6$–$C_{10}$ bicycloalkyl, $CH_2CH(CH_3)$phenyl, $CH(CH_3)CH_2CO_2R^1$, aryl, substituted aryl, or $R^4$ and $R^5$ combine to form a pyrrolidin-1-yl or piperidin-1-yl;
n is 1, 2, 3, or 4;
q is 0, 1, 2, or 3;
$R^6$ is $C_1$–$C_6$ alkyl, substituted $C_3$–$C_6$ cycloalkyl, aryl, substituted aryl, or tert-butoxy;
$R^{6'}$ is $C_1$–$C_6$ alkyl, substituted $C_3$–$C_6$ cycloalkyl, aryl, or substituted aryl;
r is 0, 1, or 2;
  $R^7$ is $C_1$–$C_6$ alkyl, phenyl, or substituted phenyl; and
  $R^8$ is hydrogen or $CO_2R^1$; or a pharmaceutical salt or solvate thereof.

10. The method according to claim 9 where the mammal is a human.

11. The method according to claim 10 where the compound of formula I is a compound where m is 0 and m' is 0 or 1 and R is at the meta position, or a pharmaceutical salt or solvate thereof.

12. The method according to claim 11 where the compound of formula I is a compound where R is $CHR^1NHR^2$ and $R^1$ is methyl, or a pharmaceutical salt or solvate thereof.

13. The method according to claim 12 where the compound of formula I is a compound where $R^2$ is 4-aminosulfonylbenzyl or 3,4,5-trimethoxybenzyl, or a pharmaceutical salt or solvate thereof.

14. The method according to claim 11 where the compound of formula I is a compound where R is $COR^3$ or $(CH_2)COR_3$, or a pharmaceutical salt or solvate thereof.

15. The method according to claim 14 where the compound of formula I is a compound where $R^3$ is (3,4,5-trimethoxyphenyl)amino or (4-aminosulfonylphenyl amino, or a pharmaceutical salt or solvate thereof.

16. The method according to claim 11 where the compound of formula I is a compound where R is $(CH_2)NR^4R^5$ and $R^4$ is hydrogen, or a pharmaceutical salt or solvate thereof.

17. The method according to claim 16 where the compound of formula I is a compound where $R^5$ is 3,4,5-trimethoxybenzoyl, 3,5-dimethoxy-4-hydroxybenzoyl, or 3,4,5-trimethoxybenzyl, or a pharmaceutical salt or solvate thereof.

18. A pharmaceutical formulation comprising a compound of formula I:

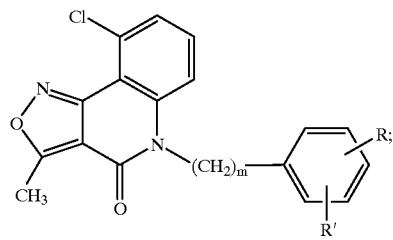

where:
R is $(CH_2)_m$, $CHR^1NHR^2$, $O(CH_2)_2NHR^2$, $(CH_2)_m$, $COR^3$, and $NHR^2$, $(CH_2)_m$, $CHR^1NR^4R^5$;
R' is hydrogen, hydroxy, or $O(C_1$–$C_6$ alkyl optionally substituted with phenyl or $C_3$–$C_7$ cycloalkyl);
m and m' are independently at each occurrence 0, 1, or 2;
  $R^1$ is independently at each occurrence hydrogen or $C_1$–$C_6$s alkyl;
  $R^2$ is hydrogen, $COR^6$, $CH_2R^{6'}$, $SO_2R^7$, or a moiety of the formula

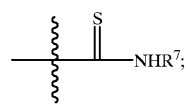

$R^3$ is hydrogen, hydroxy, $C_1$–$C_6$ alkoxy, an amino ester, an amino acid, or $NR^4R^5$;
$R^4$ is hydrogen or $C_1$–$C_{6\ l\ alkyl}$;
$R^5$ is hydrogen, $C_1$–$C_6$ alkyl, $C_6$–$C_{10}$ bicycloalkyl, $CH_2CH(CH_3)$phenyl, $CH(CH_3)CH_2CO_2R^1$, aryl, substituted aryl, or $R^4$ and $R^5$ combine to form a pyrrolidin-1-yl piperidin-1-yl;
n is 1, 2, 3, or 4;
is 0, 1, 2, or 3;
R is $C_1$–$C_6$-alkyl, substituted $C_3$–$C_6$ cycloalkyl, aryl, substituted aryl, or tert-butoxy;
$R^6$ is $C_1$–$C_6$ alkyl, substituted $C_3$–$C_6$ cycloalkyl, aryl, or substituted aryl;
r is 0, 1, or 2;
  $R^7$ is $C_1$–$C_6$ alkyl, phenyl, or substituted phenyl; and
  $R^8$ is hydrogen or $CO_2R^1$; or a pharmaceutical salt or solvate thereof.

* * * * *

UNITED STATES PATENT AND TRADEMARK OFFICE
CERTIFICATE OF CORRECTION

PATENT NO.    : 6,369,070 B1
DATED         : April 9, 2002
INVENTOR(S)   : Gruber, Joseph M. et al.

It is certified that error appears in the above-identified patent and that said Letters Patent is hereby corrected as shown below:

<u>Column 67,</u>
Line 20, delete "R is $(CH_2)_m$, $CHR^1NHR^2$, $O(CH_2)_2NHR^2$ $(CH_2)_m$, $COR^3NHR^2$, and $(CH_2)_m$, $CHR^1NH^4R^5$;" and insert -- R is $(CH_2)_m$, $CHR^1NHR^2$, $O(CH_2)_2NHR^2$, $(CH_2)_m$, $COR^3$, $NHR^2$, and $(CH_2)_m$, $CHR^1NH^4R^5$; -- therefor.
Line 67, delete "$(CH_2) COR_3$," and insert -- $(CH_2) COR^3$, -- therefor.

<u>Column 68,</u>
Line 3, delete the word "(4-aminosulfonylphenyl amino," and insert -- (4-aminosulfonylphenyl) amino, -- therefor.
Line 38, delete "$C_1-C_6S$" and insert -- $C_1-C_6$ -- therefor.
Line 50, delete "$C_1-C_{6\ 1\ alkyl}$;" and insert -- $C_1-C_6$ alkyl; -- therefor.
Line 56, insert -- q -- at the beginning of the line therefor.

Signed and Sealed this

First Day of October, 2002

Attest:

Attesting Officer

JAMES E. ROGAN
Director of the United States Patent and Trademark Office